US010390812B2

(12) United States Patent
Hardenbrook

(10) Patent No.: US 10,390,812 B2
(45) Date of Patent: Aug. 27, 2019

(54) TWO-STAGE SPINAL ACCESS ASSEMBLY

(71) Applicant: Mitchell A. Hardenbrook, Hopkinton, MA (US)

(72) Inventor: Mitchell A. Hardenbrook, Hopkinton, MA (US)

(73) Assignee: MH BROOK, INC., Hopkinton, MA (US)

( * ) Notice: Subject to any disclaimer, the term of this patent is extended or adjusted under 35 U.S.C. 154(b) by 290 days.

(21) Appl. No.: 14/457,368

(22) Filed: Aug. 12, 2014

(65) Prior Publication Data

US 2015/0209023 A1     Jul. 30, 2015

Related U.S. Application Data

(63) Continuation of application No. 14/035,915, filed on Sep. 24, 2013, now Pat. No. 8,801,608, which is a continuation of application No. 12/798,405, filed on Apr. 3, 2010, now Pat. No. 8,568,306.

(60) Provisional application No. 61/251,281, filed on Oct. 14, 2009, provisional application No. 61/211,835, filed on Apr. 3, 2009.

(51) Int. Cl.
| | |
|---|---|
| *A61B 17/02* | (2006.01) |
| *A61B 17/16* | (2006.01) |
| *A61B 17/00* | (2006.01) |
| *A61B 17/34* | (2006.01) |
| *A61B 90/50* | (2016.01) |

(52) U.S. Cl.
CPC ........ *A61B 17/0218* (2013.01); *A61B 17/025* (2013.01); *A61B 17/0206* (2013.01); *A61B 17/1671* (2013.01); *A61B 90/50* (2016.02); *A61B 2017/00261* (2013.01); *A61B 2017/0256* (2013.01); *A61B 2017/3445* (2013.01)

(58) Field of Classification Search
CPC ............ A61B 17/0218; A61B 17/0206; A61B 17/025; A61B 17/1671; A61B 19/26
USPC .......................................................... 600/235
See application file for complete search history.

(56) References Cited

U.S. PATENT DOCUMENTS

| | | | |
|---|---|---|---|
| 1,501,428 | A | 7/1924 | Wisoff |
| 4,747,394 | A | 5/1988 | Watanabe |
| (Continued) | | | |

FOREIGN PATENT DOCUMENTS

| | | |
|---|---|---|
| EP | 1815800 A1 | 8/2007 |
| WO | 9418893 A1 | 9/1994 |
| (Continued) | | |

OTHER PUBLICATIONS

Burak M. Ozgur, Henry E. Aryan, Luiz Pimenta, William R. Taylor, Extreme Lateral Interbody Fusion (XLIF): a novel surgical technique for anterior lumbar interbody fusion, Jul. 4 2006, The Spine Journal, 6, 435-443.

(Continued)

*Primary Examiner* — Ellen C Hammond
*Assistant Examiner* — Tessa M Matthews
(74) *Attorney, Agent, or Firm* — McCarter & English, LLP

(57) ABSTRACT

A sequence of access channels to provide access to a surgical site on a spine using: 1) a first retractor adapted to provide an access channel from outside the patient's body; 2) an inserted second retractor with a set of blades with a set of distal tips for insertion into tissue distal to the distal end of the first retractor; and 3) a retractor inserter for use with the second retractor.

17 Claims, 22 Drawing Sheets

(56) References Cited

U.S. PATENT DOCUMENTS

| | | | |
|---|---|---|---|
| 5,163,949 A | 11/1992 | Bonutti | |
| 5,197,971 A | 3/1993 | Bonutti | |
| 5,235,966 A | 8/1993 | Jamner | |
| 5,295,994 A | 3/1994 | Bonutti | |
| 5,323,765 A | 6/1994 | Brown | |
| 5,345,927 A | 9/1994 | Bonutti | |
| 5,443,484 A | 8/1995 | Kirsch et al. | |
| 5,599,279 A * | 2/1997 | Slotman | A61B 17/025 600/201 |
| 5,772,661 A | 6/1998 | Michelson | |
| 5,902,231 A | 5/1999 | Foley et al. | |
| 5,928,139 A | 7/1999 | Koros et al. | |
| 5,944,658 A | 8/1999 | Koros et al. | |
| 5,954,635 A | 9/1999 | Foley et al. | |
| 5,976,146 A | 11/1999 | Ogawa et al. | |
| 6,007,487 A | 12/1999 | Foley et al. | |
| 6,022,377 A | 2/2000 | Nuelle et al. | |
| 6,074,343 A | 6/2000 | Nathanson et al. | |
| 6,152,871 A | 11/2000 | Foley et al. | |
| 6,187,000 B1 | 2/2001 | Davison et al. | |
| 6,206,826 B1 | 3/2001 | Mathews et al. | |
| 6,217,509 B1 | 4/2001 | Foley et al. | |
| 6,371,968 B1 | 4/2002 | Kogasaka et al. | |
| 6,425,859 B1 | 7/2002 | Foley et al. | |
| 6,520,907 B1 | 2/2003 | Foley et al. | |
| 6,582,451 B1 | 6/2003 | Marucci et al. | |
| 6,679,833 B2 | 1/2004 | Smith et al. | |
| 6,689,053 B1 | 2/2004 | Shaw et al. | |
| 6,755,841 B2 * | 6/2004 | Fraser | A61F 2/4611 606/99 |
| 6,793,656 B1 | 9/2004 | Mathews | |
| 6,800,084 B2 | 10/2004 | Davison et al. | |
| 6,945,933 B2 | 9/2005 | Branch et al. | |
| 7,087,055 B2 | 8/2006 | Lim et al. | |
| 7,108,705 B2 | 9/2006 | Davison et al. | |
| 7,179,225 B2 | 2/2007 | Shluzas et al. | |
| 7,182,729 B2 | 2/2007 | Abdelgany et al. | |
| 7,198,598 B2 | 4/2007 | Smith et al. | |
| 7,207,949 B2 | 4/2007 | Miles et al. | |
| 7,210,485 B2 | 5/2007 | Zinkel | |
| 7,223,278 B2 | 5/2007 | Davison et al. | |
| 7,229,408 B2 | 6/2007 | Douglas et al. | |
| 7,267,690 B2 | 9/2007 | Felt | |
| 7,322,935 B2 | 1/2008 | Palmer et al. | |
| 7,427,264 B2 | 9/2008 | Nowitzke et al. | |
| 7,491,168 B2 | 2/2009 | Raymond et al. | |
| 7,494,489 B2 | 2/2009 | Roh | |
| 7,513,869 B2 | 4/2009 | Branch et al. | |
| 7,585,290 B2 | 9/2009 | Kathrani et al. | |
| 7,625,374 B2 | 12/2009 | Branch et al. | |
| 7,641,659 B2 | 1/2010 | Emstad et al. | |
| 7,641,670 B2 | 1/2010 | Davison et al. | |
| 7,645,232 B2 | 1/2010 | Shluzas | |
| 7,655,012 B2 | 2/2010 | DiPoto et al. | |
| 7,670,354 B2 | 3/2010 | Davison et al. | |
| 7,674,273 B2 | 3/2010 | Davison et al. | |
| 7,691,057 B2 | 4/2010 | Miles et al. | |
| 7,699,877 B2 | 4/2010 | Davison | |
| 7,731,737 B2 | 6/2010 | DiPoto | |
| 7,736,305 B2 | 6/2010 | DiPoto | |
| 7,749,269 B2 | 7/2010 | Peterman et al. | |
| 7,763,078 B2 | 7/2010 | Peterman et al. | |
| 7,766,930 B2 | 8/2010 | DiPoto et al. | |
| 7,776,095 B2 | 8/2010 | Peterman et al. | |
| 7,803,161 B2 | 9/2010 | Foley et al. | |
| 7,819,801 B2 | 10/2010 | Miles et al. | |
| 7,993,378 B2 | 8/2011 | Foley et al. | |
| 8,007,492 B2 | 8/2011 | DiPoto et al. | |
| 8,388,525 B2 * | 3/2013 | Poo | A61B 17/02 600/206 |
| 8,568,306 B2 | 10/2013 | Hardenbrook | |
| 8,801,608 B2 | 8/2014 | Hardenbrook | |
| 2003/0236520 A1 | 12/2003 | Lim et al. | |
| 2004/0093001 A1 * | 5/2004 | Hamada | A61B 17/02 606/190 |
| 2004/0230100 A1 * | 11/2004 | Shluzas | A61B 17/0218 600/208 |
| 2005/0075540 A1 * | 4/2005 | Shluzas | A61B 1/00149 600/203 |
| 2005/0137461 A1 * | 6/2005 | Marchek | A61B 17/025 600/220 |
| 2005/0159650 A1 * | 7/2005 | Raymond | A61B 17/02 600/201 |
| 2005/0159651 A1 | 7/2005 | Raymond et al. | |
| 2006/0004398 A1 | 1/2006 | Binder et al. | |
| 2006/0111799 A1 * | 5/2006 | Eggenberger | G06Q 40/08 700/91 |
| 2006/0142642 A1 * | 6/2006 | Lins | A61B 1/32 600/210 |
| 2006/0195017 A1 | 8/2006 | Shluzas et al. | |
| 2006/0200186 A1 | 9/2006 | Marchek et al. | |
| 2006/0217807 A1 * | 9/2006 | Peterman | A61F 2/4455 623/17.11 |
| 2006/0224044 A1 | 10/2006 | Marchek et al. | |
| 2006/0234279 A1 | 10/2006 | Miller et al. | |
| 2007/0016223 A1 | 1/2007 | Pagliuca et al. | |
| 2007/0038216 A1 * | 2/2007 | Hamada | A61B 17/02 606/53 |
| 2007/0073112 A1 | 3/2007 | Holmes | |
| 2007/0100212 A1 | 5/2007 | Pimenta et al. | |
| 2007/0208229 A1 | 9/2007 | Prusmack | |
| 2008/0161650 A1 | 7/2008 | Hestad et al. | |
| 2008/0255563 A1 | 10/2008 | Farr et al. | |
| 2008/0306481 A1 | 12/2008 | Farr et al. | |
| 2009/0005646 A1 | 1/2009 | Nowitzke et al. | |
| 2009/0012568 A1 | 1/2009 | Farr et al. | |
| 2009/0137984 A1 | 5/2009 | Minnelli | |
| 2009/0143829 A1 | 6/2009 | Shluzas | |
| 2009/0182203 A1 | 7/2009 | Hartnick et al. | |
| 2009/0216234 A1 | 8/2009 | Farr et al. | |
| 2010/0022844 A1 | 1/2010 | Mangiardi | |
| 2010/0030065 A1 | 2/2010 | Farr et al. | |
| 2010/0069783 A1 | 3/2010 | Miles et al. | |
| 2010/0076502 A1 | 3/2010 | Guyer et al. | |
| 2010/0105986 A1 | 4/2010 | Miles et al. | |
| 2010/0105987 A1 | 4/2010 | Miles et al. | |
| 2010/0113884 A1 | 5/2010 | Miles et al. | |
| 2010/0130827 A1 | 5/2010 | Pimenta et al. | |
| 2010/0174147 A1 | 7/2010 | Miles et al. | |
| 2010/0174148 A1 | 7/2010 | Miles et al. | |
| 2010/0210917 A1 | 8/2010 | Fallin et al. | |
| 2010/0228095 A1 | 9/2010 | Warren | |
| 2011/0034777 A1 * | 2/2011 | Ames | A61B 17/025 600/206 |
| 2012/0010471 A1 * | 1/2012 | Mire | A61M 29/00 600/210 |
| 2012/0158061 A1 * | 6/2012 | Koch | A61B 17/3421 606/248 |
| 2012/0226106 A1 | 9/2012 | Miles et al. | |

FOREIGN PATENT DOCUMENTS

| | | |
|---|---|---|
| WO | 03086202 A2 | 10/2003 |
| WO | 2004002323 A2 | 1/2004 |
| WO | 2006127848 A2 | 11/2006 |
| WO | 2007075375 A2 | 7/2007 |
| WO | 2010075555 A2 | 7/2010 |

OTHER PUBLICATIONS

Darren L. Bergey, Alan T. Villavicencio, Theodore Goldstein, John J. Regan, Endoscopic Lateral Transpsoas Approach to the Lumbar Spine, 2004, Spine, vol. 29, No. 15, pp. 1681-1688.

EPO Extended European Search Report on related case EP 12 17 4684 dated May 8, 2014.

Luiz Pimenta, Roberto Carlos Diaz, Luis Guerrero Guerrero, Charite lumbar artificial disc retreival: use of a lateral minimally invasive technique, J. Neurosurg Spine, Dec. 2006, vol. 5, pp. 556-561.

(56) References Cited

OTHER PUBLICATIONS

PCT International Search Report and Written Opinion dated Dec. 27, 2010, for PCT Application No. PCT/US2010/001014 which corresponds to the present application (14 Pages).

* cited by examiner

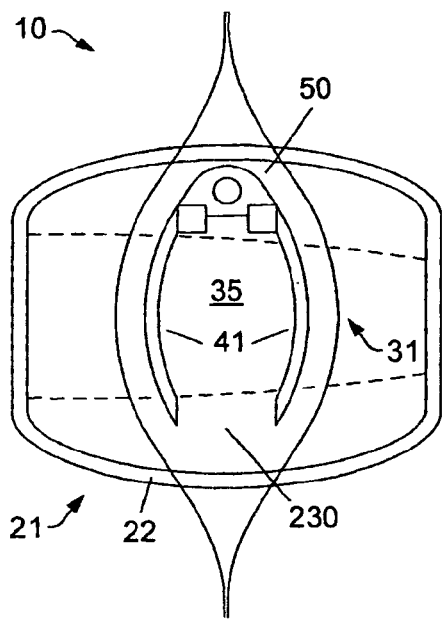
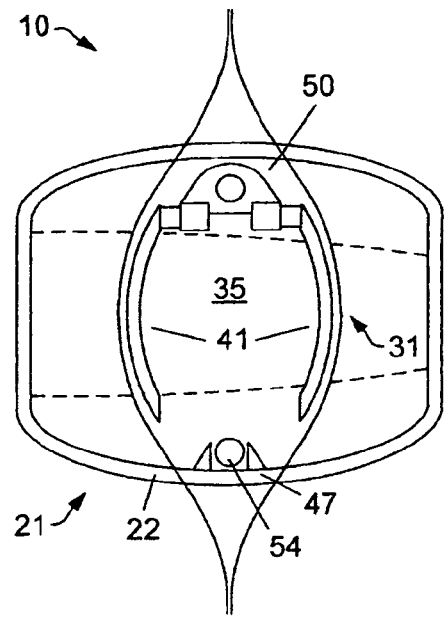
FIG. 15      FIG. 16
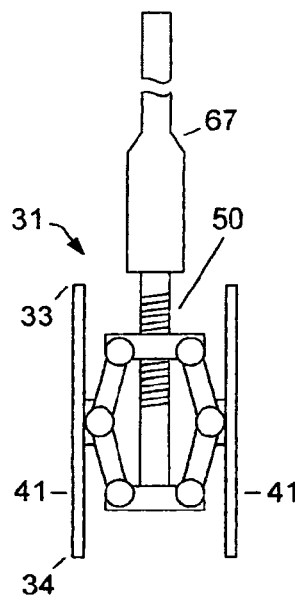
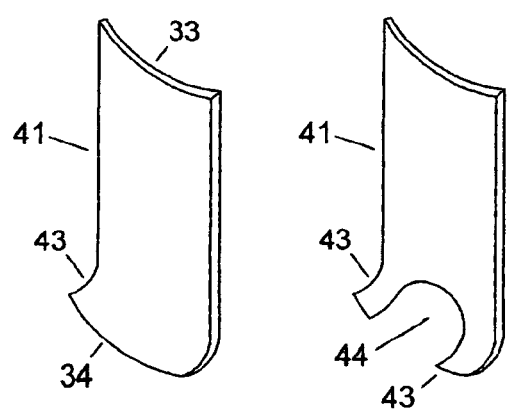
FIG. 17      FIG. 18   FIG. 19

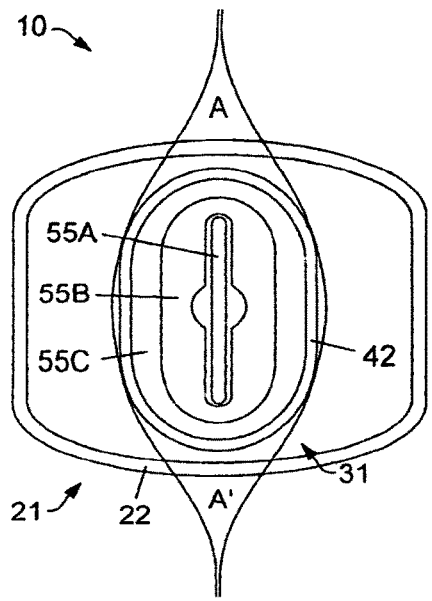
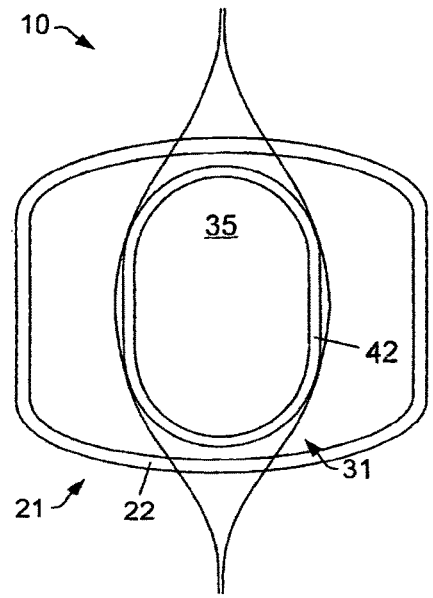
FIG. 36  FIG. 37
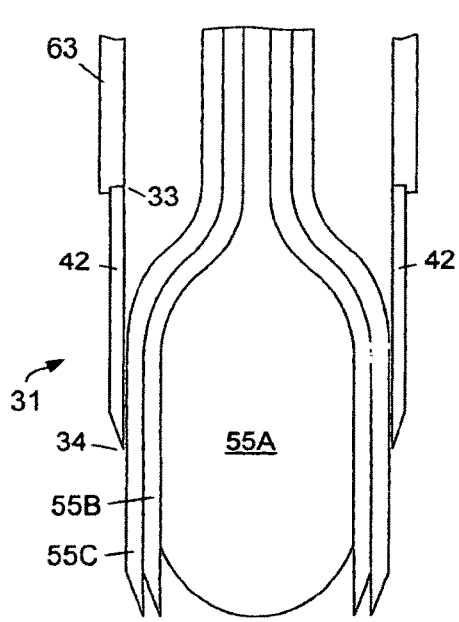
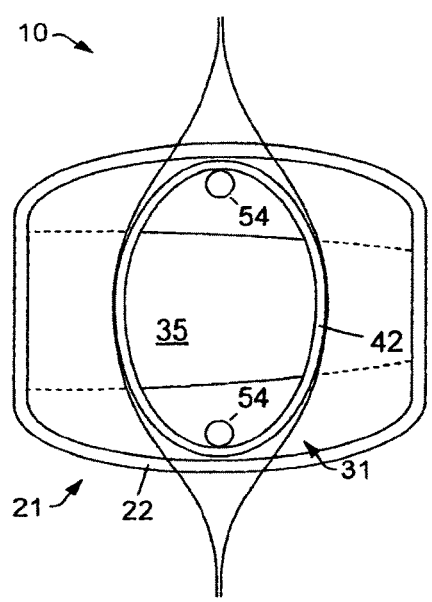
FIG. 38  FIG. 39

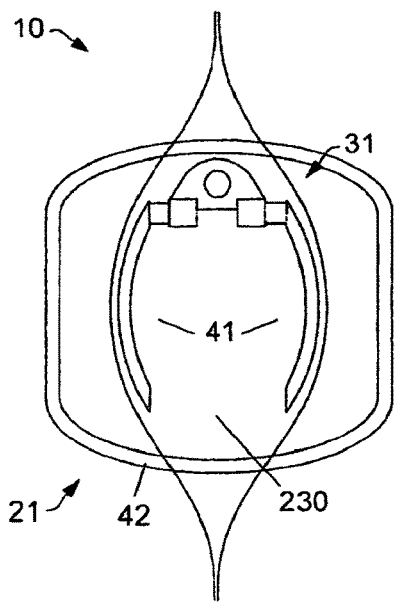
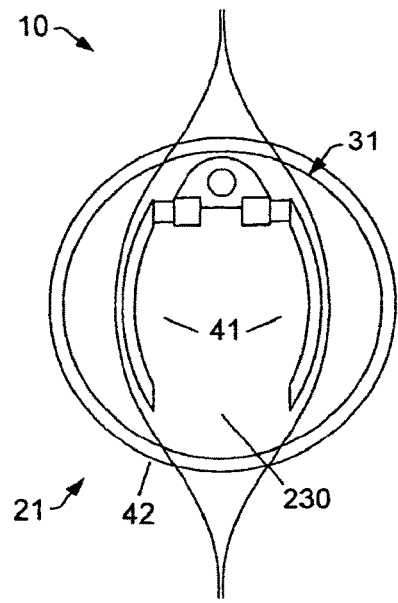
FIG. 40
FIG. 41
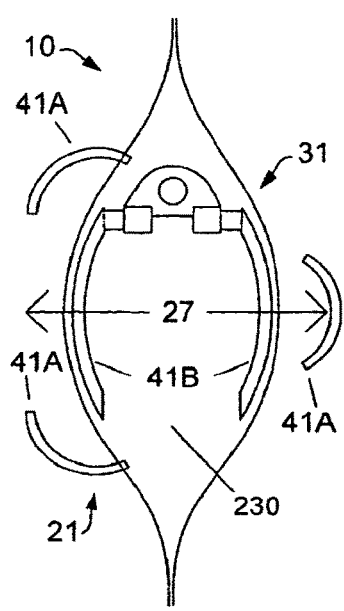
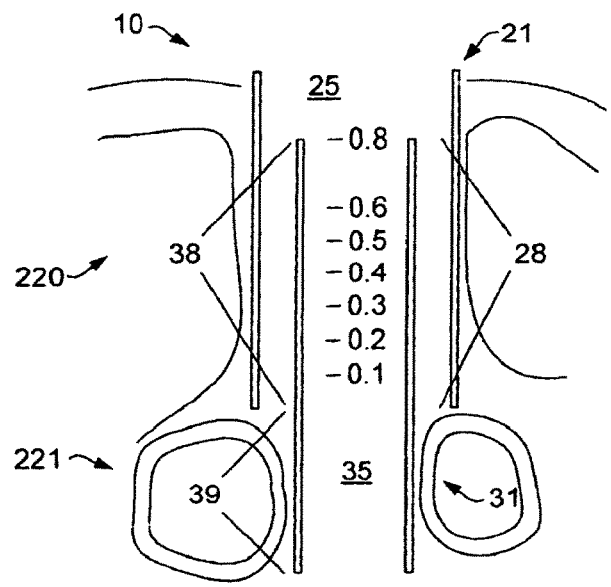
FIG. 42
FIG. 43

TWO-STAGE SPINAL ACCESS ASSEMBLY

This application is a continuation application of co-pending and commonly assigned U.S. patent application Ser. No. 14/035,915 filed Sep. 24, 2013 for Two-Stage Access Channel with Psoas Docking. The '915 application was a continuation application of then co-pending and commonly assigned U.S. patent application Ser. No. 12/798,405 for Surgical Retractor System filed Apr. 3, 2010. The '405 application claimed the benefit of two provisional applications, 61/251,281 filed Oct. 14, 2009 and 61/211,835 filed Apr. 3, 2009. All four applications are incorporated by reference.

BACKGROUND

Surgical retractors are used to provide access to a surgical site and to provide a clear view of the operating field. A retractor has one or more surfaces that contact tissues or organs in order to hold open an incision or to enlarge an anatomical space. The retracted elements may include any of various tissues or organs such as skin, muscle, nerves, blood vessels, or other tissues or organs. In some types of retractors, one or more blades (elongated laminae) serve to retract tissue, with a frame or arm or handles holding the blades at the chosen positions. The positions typically are variable during the positioning process. The blades may have a hook shape, like the letter J. Another type of retractor is a tubular retractor, which is a tube that is open at both ends. In one common embodiment, tubular retractors come in nesting sets.

Retractors are used for a wide variety of purposes in surgery. However, in some uses, conventional retractors are not entirely satisfactory. Current surgical practice emphasizes access to surgical sites via paths that are not necessarily the most direct, in order to minimize collateral damage in the process of the surgery, or to preferentially incise tissue that heals rapidly. The resulting preferred access paths can be longer or more tortuous than classical access paths, even while producing shorter recovery periods or minimizing damage to tissues.

In turn, such more complex access paths can be difficult to establish or maintain with a classical retractor. Improved retractor systems, carefully designed and fabricated to allow them to work in concert, are needed to facilitate the performance of these improved methods of surgery.

SUMMARY OF THE DISCLOSURE

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Other systems, methods, features and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 15 is a partial section end view of a surgical retractor system comprising a first retractor and a second retractor, the second retractor comprising a jackscrew and a second means for retracting that comprises a plurality of blades.

FIG. 16 a partial section end view of the surgical retractor system of FIG. 15 after expanding the second retractor.

FIG. 17 is a side view of the second retractor of the surgical retractor system of FIG. 15, with a driver engaging the jackscrew.

FIG. 18 is a perspective view of a blade having a curved portion.

FIG. 19 is a perspective view of a blade having curved portions separated by a cutout.

FIG. 36 is a partial section end view of a surgical retractor system comprising a first retractor, a second retractor, and a set of sequential dilators, the second retractor comprising a second means for retracting that comprises a tube.

FIG. 37 is a partial section end view of the surgical retractor system of FIG. 36 after removal of the sequential dilators.

FIG. 38 is a longitudinal section view of the surgical retractor system of FIG. 36 during the insertion of the tube over a final one of the set of sequential dilators.

FIG. 39 is a partial section end view of a surgical retractor system similar to that of FIGS. 36-38 after removal of the sequential dilators, the surgical retractor system including a pin.

FIG. 40 is a partial section end view of a surgical retractor system comprising a first retractor and a second retractor, the first retractor comprising a first means for retracting that comprises a tube.

FIG. 41 is a partial section end view of a surgical retractor system comprising a first retractor and a second retractor, the first retractor comprising a first means for retracting that comprises a tube.

FIG. 42 is a partial section end view of a surgical retractor system comprising a first retractor and a second retractor, the first retractor comprising a first means for retracting that comprises a plurality of blades.

FIG. 43 depicts embodiments in which first working channel distal region 28 corresponds to less than or equal to various distal-most percentages of the first working channel 25.

DETAILED DESCRIPTION

Figures 1, 2:
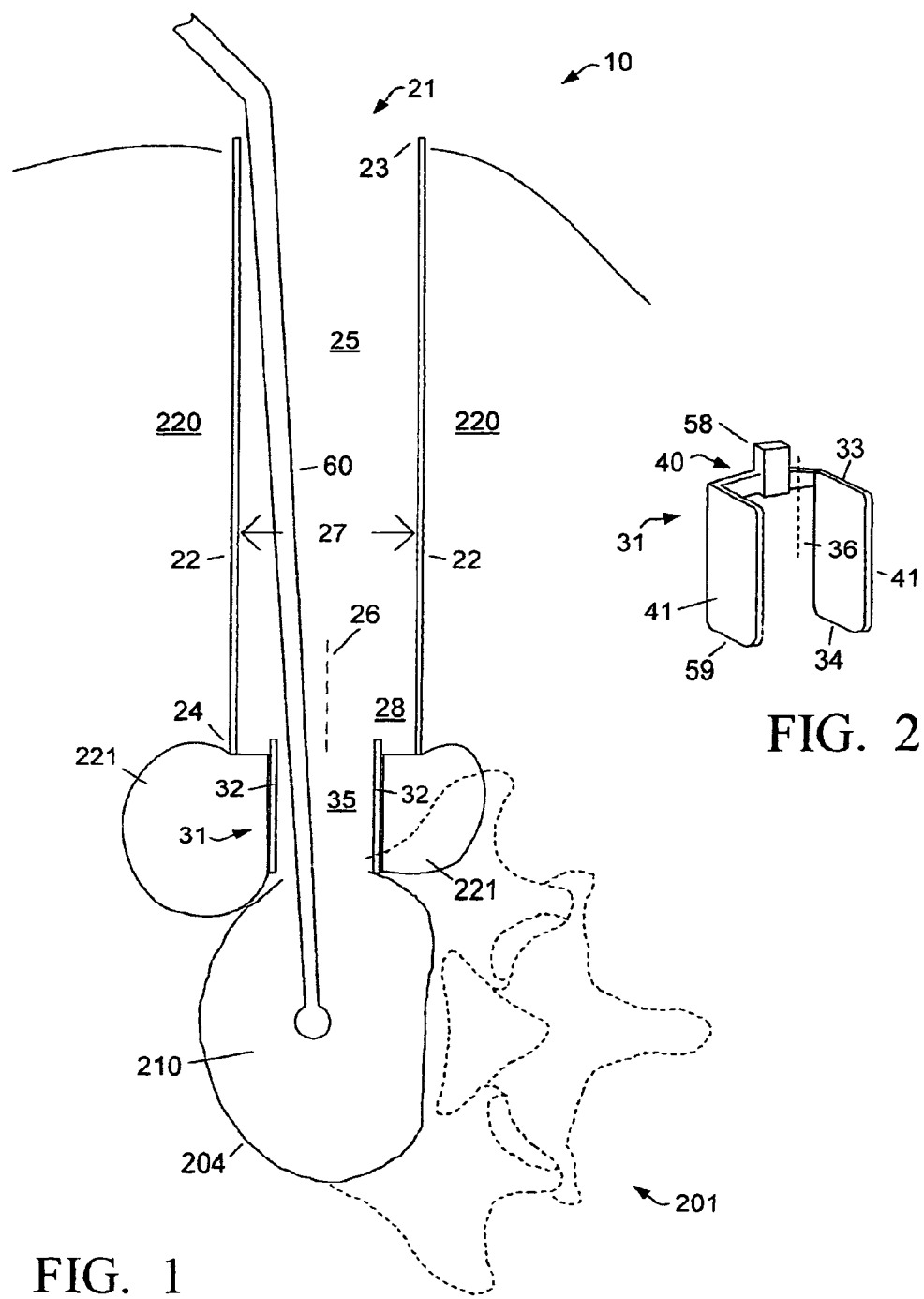
FIG. 1 is a longitudinal section view of a surgical retractor system comprising a first retractor and a second retractor.
FIG. 2 is a perspective view of the second retractor of the surgical retractor system of FIG. 1.

Reference will now be made in detail to several embodiments, examples of which are illustrated in the accompanying drawings. In this description and in the appended claims, the terms 'a' or 'an' are used, as is common in patent documents, to include "one" or "more than one". In this description and in the appended claims, the term 'or' is used to refer to a nonexclusive or, unless otherwise indicated. Various retractors are described herein, but the term "retractor" is intended to extend to any devices that embody means for the retraction of tissue, except where specifically limited. "Distal" and "proximal", unless otherwise qualified, refer to relative distance, with respect to the outside end, of the pathway made to reach the site from the beginning of the procedure, along the route of the path. A "working channel" is a functional route through a tissue or other location in the body, which typically will have its origin at least in part via an externally-applied apparatus, but which may have full, partial or no surrounding external elements when in use.

The invention describes surgical retractor systems, in which two retractors are designed and constructed, so that they may be deployed cooperatively to reliably achieve results that can only be obtained with difficulty, if at all, with a single retractor, or by use of multiple retractors that are not carefully matched. In preferred embodiments, the retractor systems will combine in ways that allow a second or distal retractor to have a wider opening, at its distal end, than the proximal openings of either retractor. This is important in many situations to provide visibility to the operative site during the procedure. It also, as described below, can provide benefits in terms of stabilizing the retractor in the operating field during the procedure.

The retractors used in the invention can be selected from any of the types of retractors currently in use, although some combinations are preferred. Generally, the system comprises a first retractor, which is characterized by having an aperture which topologically is open to the outside of the body. The "topological" designation includes both direct access via a portal in the skin or other external body surface (which will likely be the most common mode of use), but also includes access via a natural orifice, including penetration through the wall of a natural orifice, or via a temporary artificial orifice created for other purposes.

The system of the invention also includes a second retractor. The second retractor is delivered to the site of operation through the first retractor. Such a procedure is outlined in FIG. 45, where a second retractor is placed in its compact configuration (panel A) and in this folded state is delivered through a passage in a first retractor, in this case a tubular retractor, as shown in panel B. The second retractor is then opened, as shown in panel C, optionally by passing an opening device (63) through the first retractor passage. The deployed second retractor is shown in panel D. After deployment, the opening device 63 can be removed. The procedure is reversed to remove the second retractor at the end of the procedure. Note that the retractor in panel C has a different blade shape than the equivalent instruments in the other panels. Any of a variety of blade shapes are useful in the invention. The blade shape of panel D is preferred, because it is more readily deployed in a configuration in which the distal tips of the blades are separated by a distance that is greater than the relevant clearance of the first retractor through which it is passed to the operative site. This configuration is preferred because it is more stable in position, once it has been deployed, and because it increases the area which can be visualized and accessed beyond the distal opening of the first retractor.

Figure 3A:
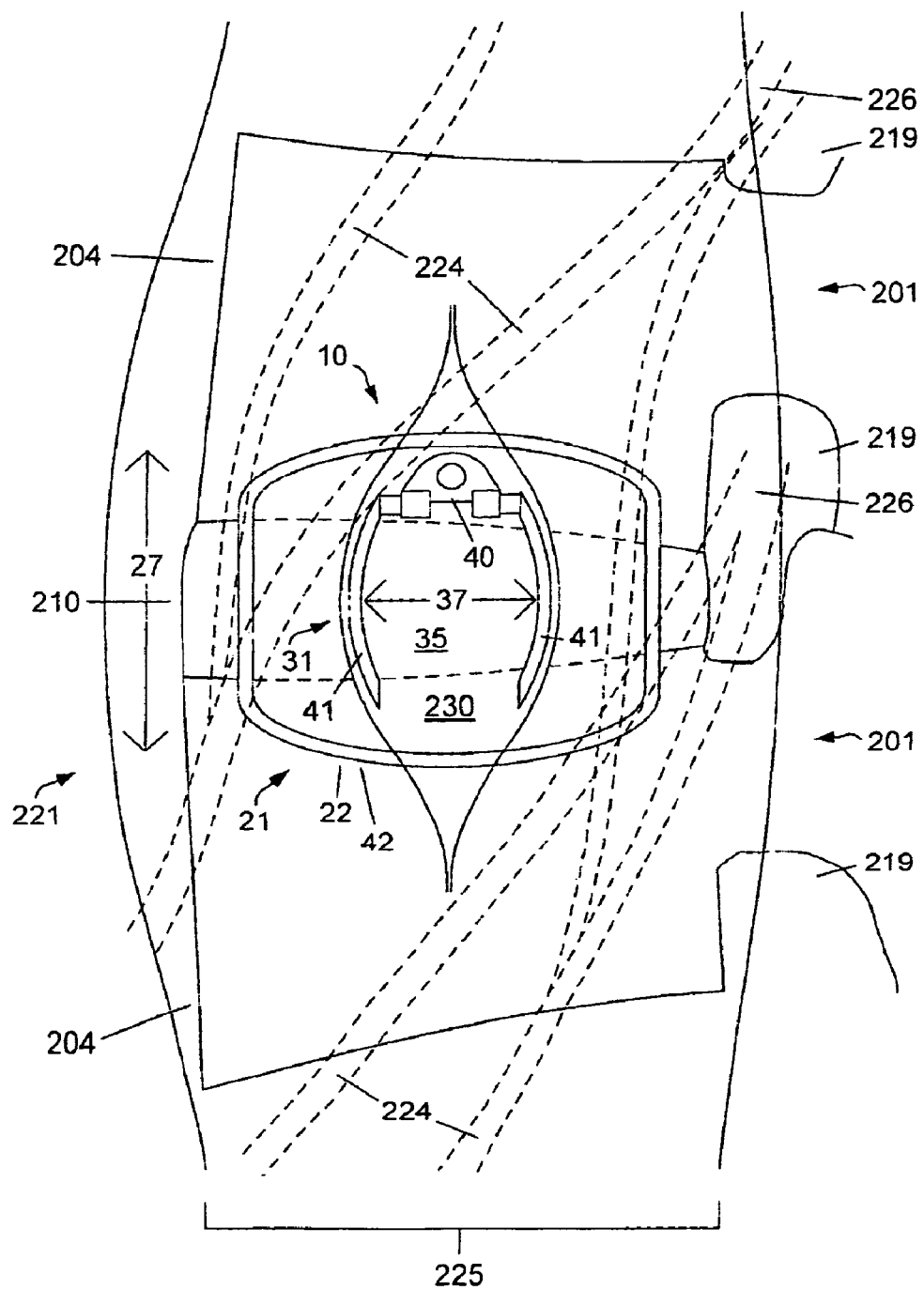
FIG. 3A is a partial section side view of a surgical retractor system similar to that of FIG. 1.
Figure 3B:
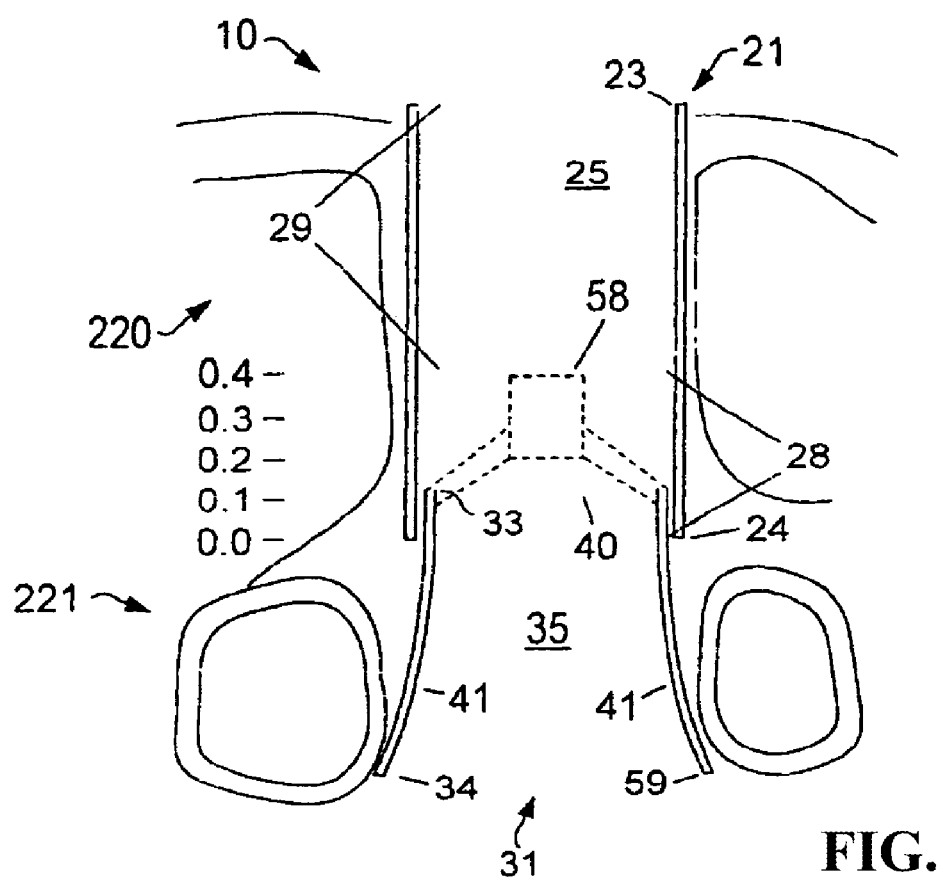
FIG. 3B is a side view of the second retractor in its deployed form.

The Figures show a variety of deployments and procedures which make the invention more readily apparent to the reader. FIG. 1 is a longitudinal section view of a surgical retractor system 10 comprising a first retractor 21 and a second retractor 31, in accordance with an embodiment. FIG. 2 is a perspective view of the second retractor 31 of a surgical retractor system 10 of FIG. 1. FIG. 3A is a lateral view from outside the body through the channels created by retractors 21 and 31 to the operative field. FIG. 3B is a longitudinal section, similar to FIG. 1, of an alternative second (distal) retractor. In each of these embodiments, the system is illustrated as performing steps useful in partially removing or otherwise treating a spinal disc.

In the embodiment of a surgical retractor system 10 shown in FIGS. 1-3, first retractor 21 serves to retract a first tissue 220 and second retractor 31 serves to retract a second tissue 221. For example, as illustrated, second tissue 221 may comprise muscle and nerves adjacent a vertebra 201 and a spinal disc 210, the vertebra 201 including a vertebral body 204. The vertebra 201 and spinal disc 210 are depicted in axial view (the view is taken along the axis of the spine) in FIG. 1, and laterally in FIG. 3. In the axial view, spinal disc 210 is superimposed upon vertebral body 204. Much of the vertebra 201 is out of the plane of the section view, and is therefore indicated using dashed lines. In the embodiment of FIGS. 1-3, the surgical site that is to be accessed and viewed is the spinal disc 210 and adjacent vertebrae 201 within a spine.

First retractor 21 comprises a first means for retracting. In the FIG. 1-3 embodiments, the first means for retracting comprises a tube 22 having proximal end 23 and distal end 24. The tube 22 defines a first working channel 25 there through. The first working channel 25 extends between the first tube proximal end 23 and the first distal end 24. The first working channel 25 includes a distal region 28 of the first working channel. In one embodiment, the distal region 28 comprises no more than about 40% of the length of first working channel 25.

Second retractor 31 in this embodiment, as shown in FIGS. 1, 2 and 3, comprises a frame 40 (out of plane in FIG. 1) and a second means for retracting 32. In the FIG. 1-3, 3B embodiments, second means for retracting 32 comprises a plurality of blades 41 (2, 3, 3B). The frame 40 (FIG. 2, 3, 3B) comprises a means for expanding the second retractor 31. The plurality of blades 41 are attached to the frame 40. (Frame 40 is indicated in FIGS. 2 and 3; frame 40 is out of the plane of section in FIG. 1). The plurality of blades 41 includes, as shown in FIG. 3B, a second means for retracting proximal end 33 and a second means for retracting distal end 34. The plurality of blades 41 defines a second working channel 35 there through. The second working channel 35 extends between the second means for retracting proximal end 33 and the second means for retracting distal end 34. The second retractor 31 has a second retractor proximal end 58 and a second retractor distal end 59.

Second retractor 31, as shown in FIG. 2 or 3B, is dimensioned to be insertable through the first working channel 25. Second retractor 31 is positionable vicinally to the distal end 24 of the first retractor, with the second retractor distal end 59 positioned distal to the first working channel 25, and with the second retractor proximal end 58 positioned distal to the first working channel 25 or within the first working channel distal region 28.

FIG. 3A is a partial section end view of a surgical retractor system 10 similar to that of FIG. 1. In the embodiment of FIG. 3A, first means for retracting 22 is a tube 42 with a cross-sectional shape that is a rounded rectangle, and a second retractor 31 has a plurality of blades 41 serving as a means for retracting. Two vertebrae 201 and a spinal disc 210 are depicted in lateral view. Each vertebra 201 includes a vertebral body 204. In the embodiment of FIG. 3, the second tissue 221 that is retracted by the second retractor 31 includes the psoas major muscle 225 and various nerves 224. The psoas major muscle 225 is an elongate muscle that runs laterally to the lumbar region of the spine, roughly parallel to the spine axis. In FIG. 3A and other figures herein, the psoas major muscle 225 is depicted as transparent, revealing the outlines of the vertebra 201 and spinal disc 210. In the embodiments of FIGS. 1-3, second retractor 31 is inserted into an opening 230, having a lenticular-shaped outline, in the psoas major muscle 225. Those of skill in the art will recognize that the term iliopsoas is sometimes used as a term for a combination of the psoas major muscle and the relatively shallow layer of the iliacus.

Nerves 224 (depicted as dashed lines) originate at spinal nerve roots 226. Each spinal nerve root 226 emerges from the spine through an intervertebral foramen 219, which is a passage between the posterior portions of adjacent vertebrae 201. Nerves 224 pass through, under, or over the psoas major muscle 225; the exact route of the nerves 224 varies with the spine level and the individual patient.

As described in connection with FIGS. 1-2, second retractor 31 is disposed adjacent the distal end 24 of the first means for retracting 21. In some embodiments, the second retractor distal end 59 is positioned distal to the first working channel 25 (see FIG. 2) and the second retractor proximal end 58 is also positioned distal to the first working channel 25, so that the entire second working channel 35, defined by second means for retracting 32, is distal to the first working channel 25. Embodiments of this type are described in connection with FIGS. 4 and 5. In other embodiments, such as that of FIG. 1, the second retractor distal end 59 is positioned distal to the first working channel 25 and the second retractor proximal end 58 is positioned within the first working channel distal region 28. In these embodiments, the second working channel 35, defined by second means for retracting 32, is disposed partially within first working channel distal region 28 and partially distal to first working channel 25.

The distal region 28 of the first channel usually corresponds to the distal-most 40 percent or less of the first working channel 25, as described in connection with FIGS. 1-2. FIG. 3B depicts an embodiment in which first working channel distal region 28 corresponds to the distal-most 40 percent of the first working channel 25. In this embodiment, first working channel proximal region 29 corresponds to the remaining 60 percent of first working channel 25. Second retractor proximal end 58 is positioned within the first working channel distal region 28. Thus, second working channel 35 does not extend into first working channel proximal region 29.

In other embodiments, first working channel distal region 28 may correspond to other distal-most percentages of the first working channel 25, but preferably the distal-most percentage is less than or equal to 40 percent. In the FIG. 1 embodiment, for example, first working channel distal region 28 corresponds to approximately the distal-most three (3) percent of first working channel 25. In the FIG. 3B embodiment, for example, first working channel distal region 28 corresponds to approximately the distal-most 20 percent of first working channel 25. A scale within FIG. 3B indicates several distal-most percentages of first working channel 25. The percentages are indicated as fractions.

In FIGS. 1-3B, the positioning of second retractor 31 adjacent to first means for retracting distal end 24 results from the advancing of second retractor 31 through first working channel 25, as described in connection with FIGS. 1-3B. Second retractor 31 and second working channel 35 temporarily pass through first working channel proximal region 29 (FIG. 3B) while en route to the final position adjacent distal end 24.

First means for retracting 22 may comprise any structure that is capable of defining a first working channel 25. For example, first means for retracting 22 may comprise tube 42 (FIG. 3) or a plurality of blades 41 (FIG. 3B). In the embodiment of FIG. 3, first means for retracting 22 comprises a tube 42 having a cross-sectional shape that is a rounded rectangle. FIGS. 40-42 below depict other embodiments of first means for retracting 22.

Second means for retracting 32 may comprise any structure that is capable of defining a second working channel 35. Second means for retracting 32 may comprise, for example, a plurality of blades 41 or a sleeve 57 or a tube 42. In the embodiment of FIG. 3, second means for retracting 32 comprises a plurality of blades 41. FIGS. 15-39 as described below depict various embodiments of second means for retracting 32

A tool 60 that is received within first working channel 25 and within second working channel 35, for example as illustrated in FIG. 1, may be any type of tool that may be used to probe, manipulate, or view the surgical site of interest. For example, tool 60 may be a cutting instrument or grasping instrument, or a means for irrigating or suctioning the surgical site, or a type of inserter for installing an implant or prosthesis, or a driver for transmitting pounding force or rotational force, or an endoscope. The tool 60 may comprise a plurality of tools 60 that are received simultaneously or sequentially within first working channel 25 and second working channel 35.

First retractor 21 is sufficiently large to receive the tool 60 through the first working channel 25 and for advancing second retractor 31 through the first working channel 25. In some embodiments, first retractor 21 may be relatively large in order to improve visibility or to facilitate the use of tools 60 or to facilitate the advancing of a prosthetic implant through first working channel 25. In one example, as illustrated in FIG. 3, a rectangular or oval tube 42 for use in a lateral approach to the spine may have a 12 centimeter length, 42 millimeter width, and 35 millimeter depth. In other embodiments, the depth and width may be greater than or equal to 10, 15, 20, or 25 millimeters or more. In an embodiment with a relatively long first retractor 21, as in the FIG. 1-3 embodiment, transverse dimensions greater than or equal to 20 or 25 millimeters may be advantageous. First retractor 21 may be tapered along its length.

Second retractor 31 is sufficiently large to allow receiving the tool 60 through the second working channel 35 and, in some embodiments, to allow receiving a prosthetic implant through second working channel 35. In one example, second retractor 31 may have a 32 mm width and an 18 mm depth, suitable for receiving a prosthetic implant that is relatively wide, and also suitable for being received within an oval or rectangular first retractor 21.

Figure 14:
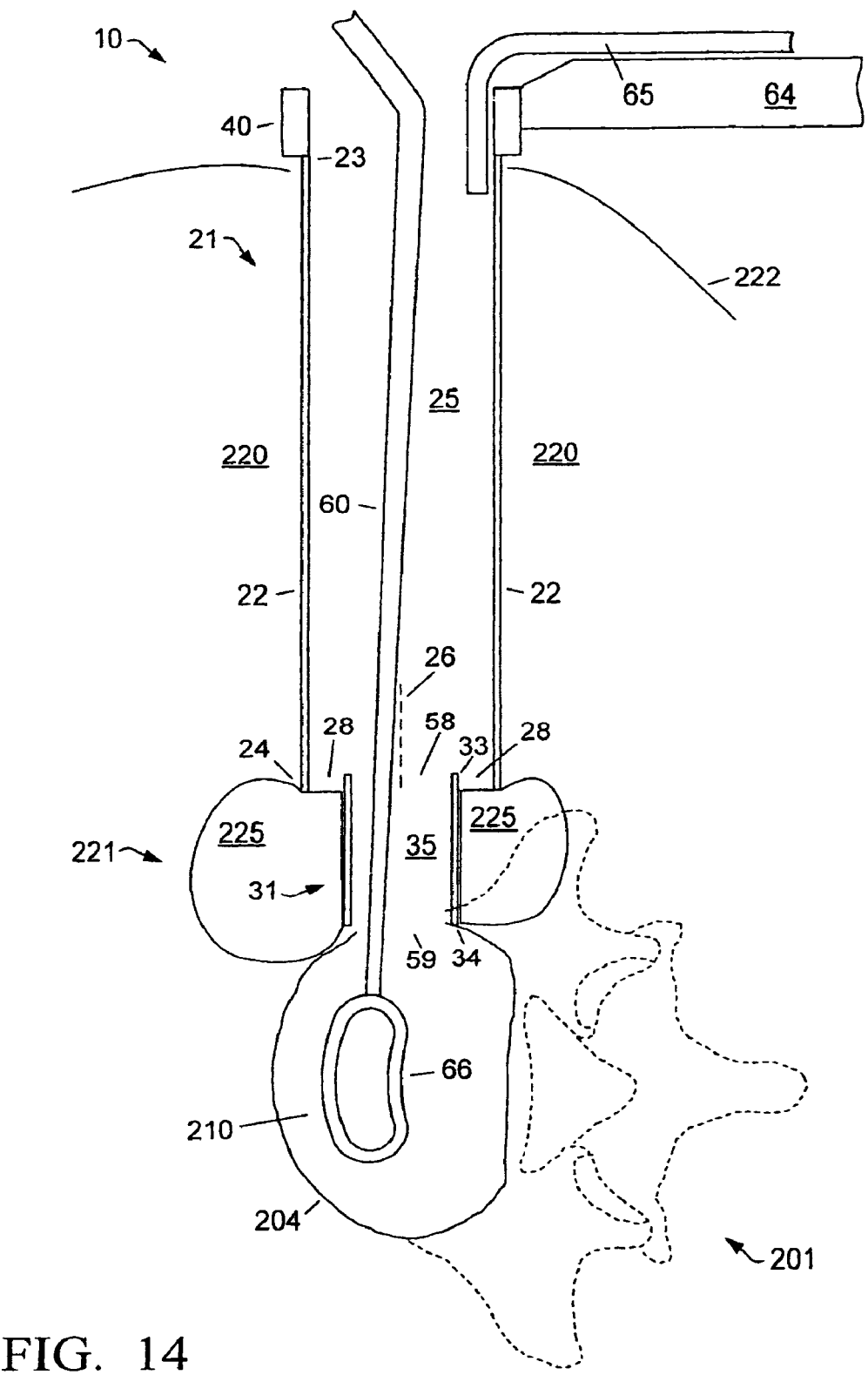
FIG. 14 is a longitudinal section view of a surgical retractor system comprising a first retractor and a second retractor after the inserting of the second retractor into the second tissue.

In some embodiments, a prosthetic implant may be installed at a surgical site that is accessed using a surgical retractor system 10 as described herein. The prosthetic implant may be any type of implant for installation at any anatomical location. For example, the prosthetic implant may be an intervertebral spacer 66 as depicted in FIG. 14. In such embodiments, the first working channel 25 is capable of receiving the prosthetic implant (e.g. an intervertebral spacer 66) and the second working channel 35 is capable of receiving the prosthetic implant. The prosthetic implant (e.g. an intervertebral spacer 66) is advanced through the first working channel 25 and through the second working channel 35 and installed at the surgical site of interest. In one example, an intervertebral spacer 66 for use in a lateral approach may have a 35 millimeter length, a 20 millimeter width, and a height of 15 millimeters.

The prosthetic implant may have fixed dimensions, or it may be expandable after arrival at the surgical site, or the prosthetic implant may be a modular implant comprising plural modules that are advanced sequentially and then joined together at the surgical site. U.S. Pat. No. 7,267,690 issued to Felt describes some examples of modular implants for use in a surgical site that is a spinal disc 210.

In some embodiments, the first retractor 21 may be expanded during or after its insertion into the first tissue 220. The first working channel diameter 27 means the diameter after the expanding is complete and the first working channel 25 is ready to receive the tool 60 and is ready for advancing of the second retractor 31. Similarly, the second working channel diameter 37 means the diameter after any expanding of second retractor 31 is complete.

Figure 4:
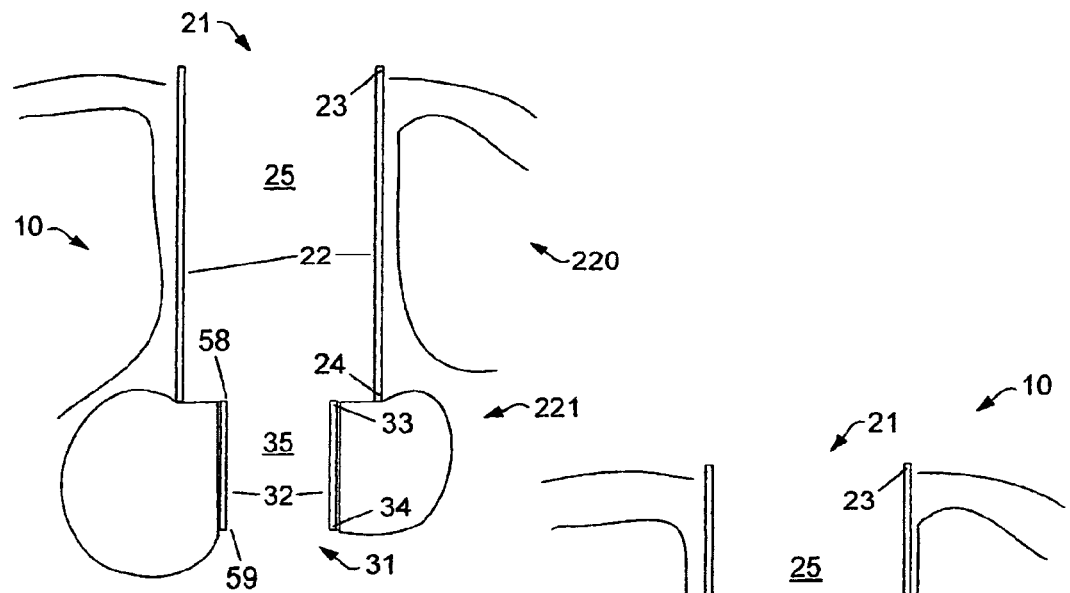
FIGS. 4, 5 and 6 are longitudinal section views of a surgical retractor system comprising a first retractor and a second retractor

FIG. 4 shows a surgical retractor system 10 comprising a first retractor 21 and a second retractor 31. In the embodiment of FIG. 4, the second working channel's proximal end 58 is positioned distal to the first working channel 25. In the embodiments of FIGS. 1 and 4, first retractor 21 is docked at a proximal surface of the second tissue 221.

Figure 5:
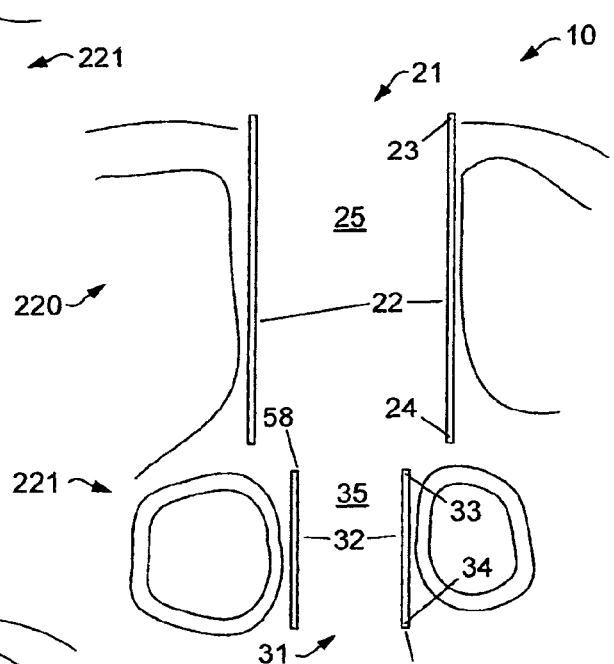

FIG. 5 shows a surgical retractor system 10 comprising a first retractor 21 and a second retractor 31. In the embodiment of FIG. 5, the second working channel proximal end 58 is positioned distal to the first working channel 25. In the FIG. 5 embodiment, first retractor 21 is not docked at a proximal surface of the second tissue 221; there is a gap between first means for retracting distal end 24 and the second tissue 221.

Figure 6:
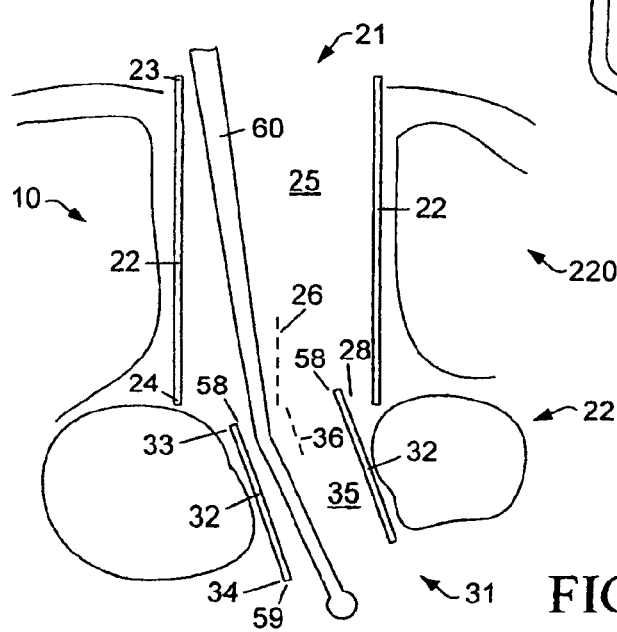

FIG. 6 shows a surgical retractor system 10 comprising a first retractor 21 and a second retractor 31. In the FIG. 6 embodiment, the second working channel 35 is at an angle with respect to the first working channel 35. Hence, the proximal end 58 of the second channel 35 is positioned partially distal to the first working channel 25 and partially within the first working channel distal region 28. Nevertheless, first working channel distal end axis 26 is sufficiently aligned with second working channel proximal end axis 36 to permit the receiving of a tool 60 simultaneously in the first working channel 25 and in the second working channel 35.

The range of overlap of the second retractor with respect to the first retractor is variable, as is shown in FIGS. 4, 5, and 6. It is preferred in many situations that there be at least some overlap between the retractors, for example in the range of about 5% to 40% overlap, in order to provide a functional pivot point. A pivot point, in this context, is an arrangement of retractors which allows relative pivoting between the first and second retractor (in terms of alignment of their axes, for example), so that the general direction of the path to the ultimate target need not lie along a single axis. Preferably, the pivot point is deep in the tissue, for example for allowing optimal visualization of the target site. However, an actual physical overlap of the first and second retractors, as shown in FIGS. 4 and 6, is not required. The same effect can be produced in the arrangement of FIG. 5, wherein there is no physical overlap of the retractors, but an alignment is preserved during pivoting by the proximity of surrounding tissues.

In an alternative embodiment, shown in FIG. 36-38, the surgical retractor system 10 may comprise a set of sequential dilators 55, shown here as 55 A-C, with the first means for retracting 22 being sized for insertion over a final one of the set of sequential dilators 55. Similarly, surgical retractor system 10 may comprise a set of sequential dilators 55, with the second means for retracting 42 being sized for insertion over a final one of the set of sequential dilators 55. A set of sequential dilators 55 may be used with any type of first means for retracting 22 or second means for retracting 32, such as a plurality of blades 41 or a tube 42. The embodiment of FIGS. 36-38 depicts an example of a surgical retractor system 10 that comprises a set of sequential dilators 55. In the FIG. 36-38 embodiment, a first one 55A of the set of sequential dilators 55 may comprises a spatula. In other embodiments, a first one 55A of a set of sequential dilators 55 may be any type of blunt dissector, such as a cylindrical rod.

Surgical retractor system 10 embodiments may be used in various anatomical locations. Similarly, method embodiments described herein may be used in various anatomical locations. Thus, the first tissue 220 and the second tissue 221 that are to be retracted may be any type of tissues in any anatomical location. While many of the system embodiments and method embodiments described herein are described in connection with spine surgery, surgical retractor system 10 and various methods described herein may be used for retracting any combination of a first tissue 220 and a second tissue 221. For example, first tissue 220 and second tissue 221 may be tissues within the brain, head, neck, thorax, pelvis, or abdomen.

Passage may be through tissue or through space. Any organ with a cavity that can be passed through to access tissues to be retracted may be treated by the devices and methods of the invention. As an example, the pleural cavity could be first tissue 220 and a great vessel could be a great vessel. First tissue 220 and second tissue 221 may be regions within a single organ or tissue. For example, first tissue 220 and second tissue 221 may be a first region and a second region within a single muscle, the first region being relatively free of sensitive elements such as nerves, the second region including one or more sensitive elements such as nerves.

The general attributes of surgical retractor system 10 that are described in connection with the embodiments of FIGS. 1-6 apply also to other embodiments. The description of those general attributes is not repeated for each embodiment described herein.

Figure 7:
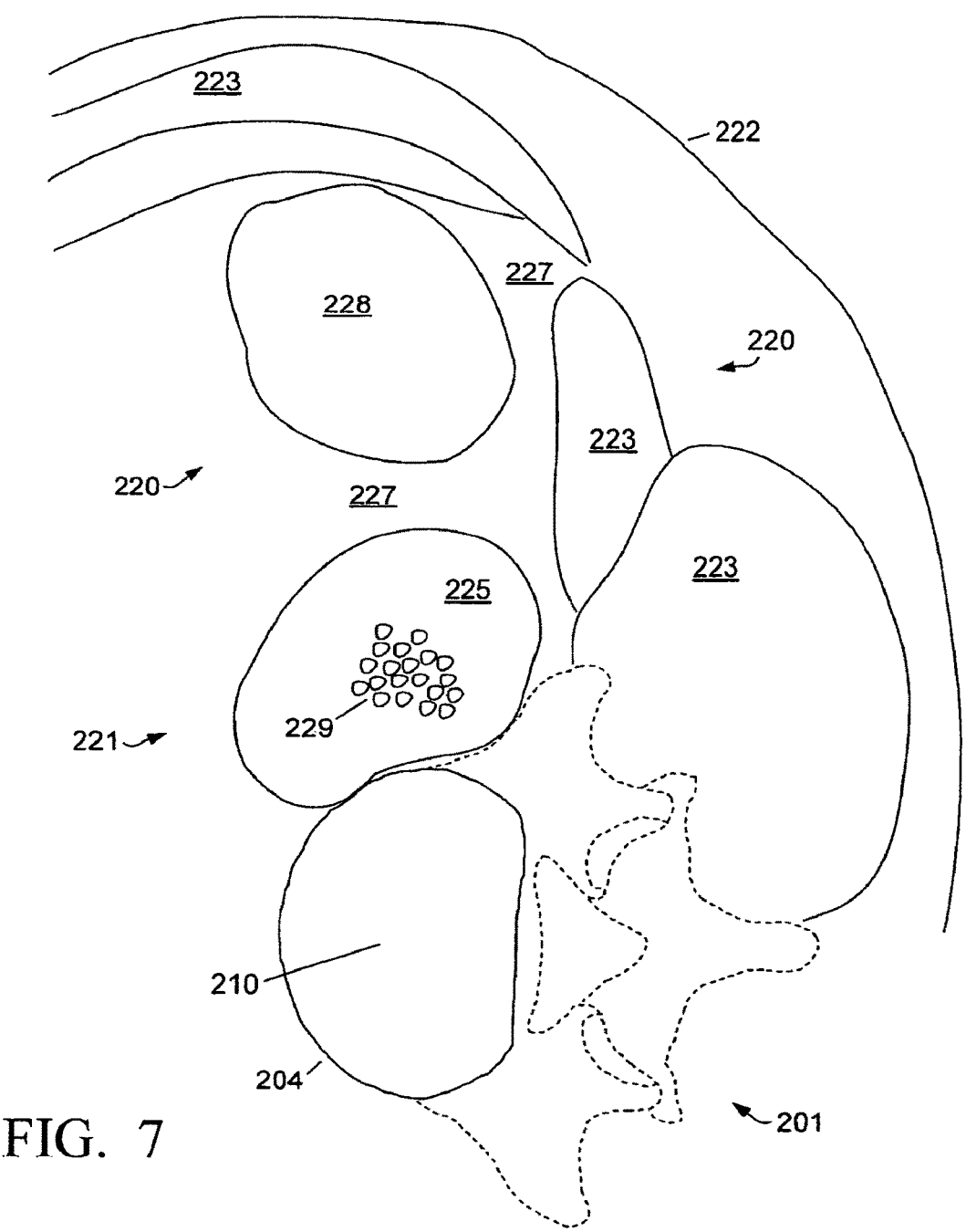
FIG. 7 is a transverse section view of the trunk of a human, the view including a vertebra and various soft tissues and organs.

FIG. 7 is a transverse section view of the trunk of a human, the view including a vertebra 201 and a spinal disc 210 within the spine and also various soft tissues and organs. The spinal disc 210 and the vertebra 201, which includes vertebral body 204, are depicted in axial view, as in FIG. 1. In this axial view, spinal disc 210 is superimposed upon vertebral body 204. Spine surgery may employ any of various approaches to the spine such as an anterior or posterior or lateral approach. In FIG. 7, anterior is to the left of vertebra 201, posterior is to the right of vertebra 201, and lateral is above or below the vertebra 201, each in the plane of the paper.

Figure 8:
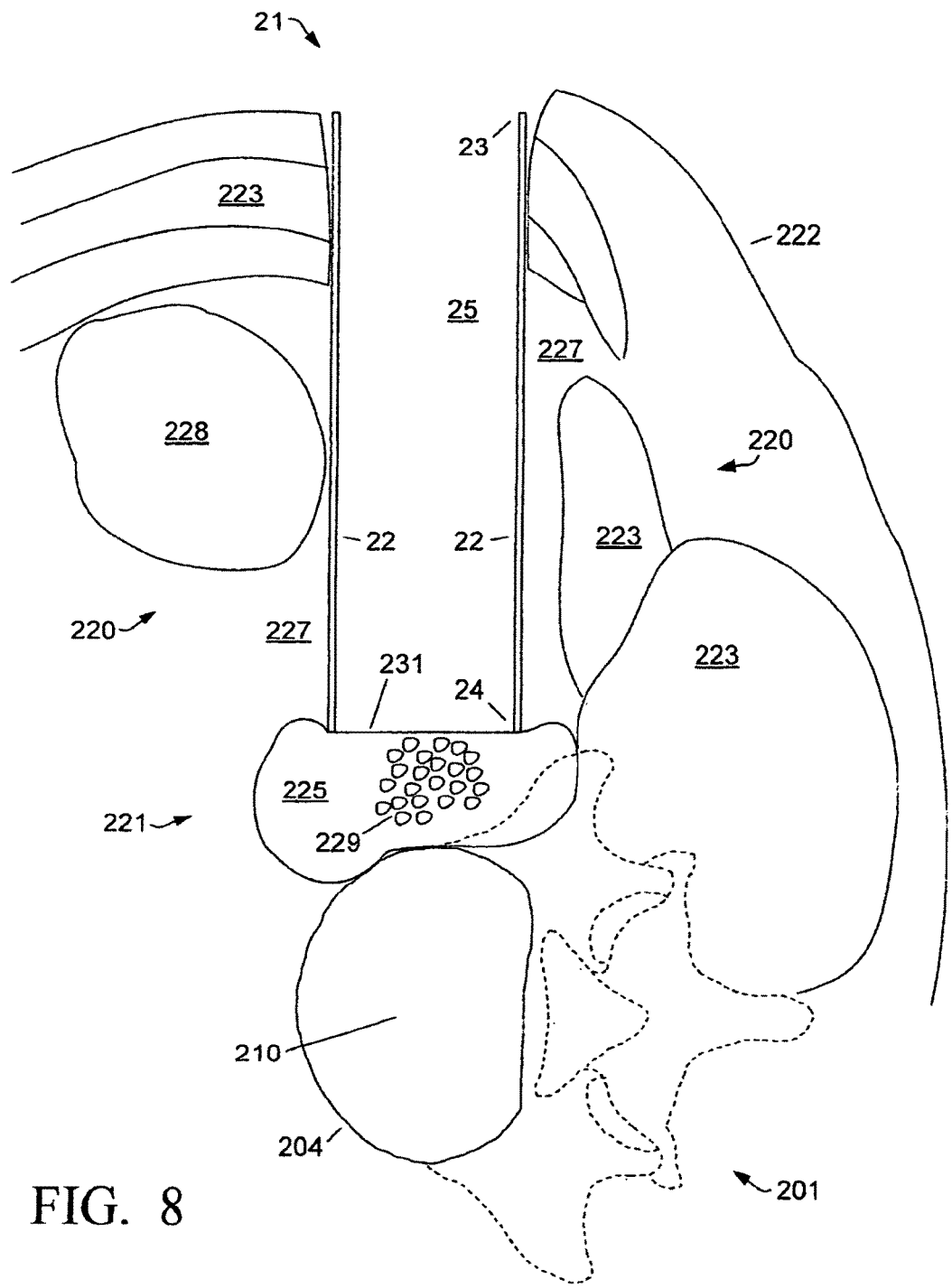
FIG. 8 is a longitudinal section view of a first retractor after the inserting of the first retractor into a first tissue.

For a lateral approach to the spine at the level depicted in FIG. 7, the first tissue 220 that is to be retracted includes skin 222, muscles 223, and a portion of the intestines 228, as shown in FIG. 8. Retraction of first tissue 220 enlarges the retroperitoneal space 227. For a lateral approach, the second tissue 221 that is to be retracted includes the psoas major muscle 225 as well as various nerves 224. Nerves 224 are depicted in FIG. 3, as structures outlined by dashes. In FIG. 3, the nerves depicted have been avoided or retracted from the path of the channel 21. Within the psoas major muscle 225, the elongate muscle fibers 229, shown here in cross section, run roughly parallel to the spine axis. In the transverse section view of FIG. 7, a portion of the muscle fibers 229 are depicted as small circles (cross-sectioned muscle fibers 229) within the psoas major muscle 225.

For spine surgery, a patient may be positioned in a particular way in order to facilitate the surgery. For a lateral approach to the spine, the patient is typically positioned so that the psoas major muscle 225 is stretched and thinned compared to the cross-sectional profile depicted in FIG. 7. FIG. 1 and FIGS. 8-14 depict the psoas major muscle 225 in a stretched and thinned configuration.

In FIGS. 8-14, a first method for accessing a surgical site is described. Broadly, the method comprising a series of steps, the method comprising:

(a) inserting a first retractor 21 into a first tissue 220 to retract the first tissue 220, the first retractor 21 including a first retractor distal end 24 and a first working channel 25, the first working channel 25 including a first working channel distal region 28 (see FIG. 14);

(b) advancing a second retractor 31 (FIG. 13-14) through the first working channel 25, the second retractor 31 including a second retractor distal end 34;

(c) inserting the second retractor 31 into a second tissue 221 to retract the second tissue 221 while positioning the second retractor 31 adjacent the first retractor distal end 24, wherein the positioning of the second retractor 31 includes positioning the second retractor proximal portion 38 to be external to the first working channel 25 or to be within the first working channel distal region 28, wherein the first retractor 21 remains proximal to the second tissue 221 during the inserting of the second retractor 31.

FIGS. 8-14 depict such a series of steps performed during the particular example of the creation of an access route from the skin to the interior of a vertebral disk. This method may be performed using a surgical retractor system such as the surgical retractor system embodiments described herein. The surgical retractor system 10 may comprise, in addition to a first retractor 21 and a second retractor 31, other elements such as a blunt dissector 61 and an inserter 63 for manipulating the second retractor 31. In the embodiment of FIGS. 8-14, the surgical site that is to be accessed is a spinal disc 210 and adjacent vertebra 201 within a spine, and the approach to the spine is a lateral approach. Fluoroscopy may be used during the performance of the method, with the patient positioned on a radiolucent surgical table.

In one embodiment, for inserting of a first retractor 21 into a first tissue 220 (step a), an incision is made in the skin 222 and the muscles 223 of the abdominal wall are split. The first retractor 21 is inserted through the incision and through the split muscles 223, passing into the retroperitoneal space 227 and staying posterior to the intestine 228. The first retractor 21 is then re-oriented so that it is directed towards the vertebral body 204 and the overlying psoas major muscle 225.

FIG. 8 is a longitudinal section view of a first retractor 21 after the inserting of the first retractor 21 into a first tissue 220 to retract the first tissue 220, in accordance with an embodiment. The first retractor 21 includes a first retractor distal end 24 and a first working channel 25. The first working channel 25 includes a first working channel distal region 28 (also see FIG. 1, 14). The first retractor distal end 24 is the same as the first means for retracting distal end 24 described in connection with other Figures herein.

The embodiment of FIG. 8 includes a step of docking the first retractor 21 at a proximal surface 231 of the second tissue 221 prior to performing other steps such as advancing a second retractor 31 through the first working channel 25. The docked first retractor 21 is seated firmly against the proximal surface 231 of the second tissue 221, which in this embodiment is the psoas major muscle 225. In other embodiments, such as the embodiment of FIG. 5, the first retractor 21 may not be docked at the second tissue 221.

Figure 9:
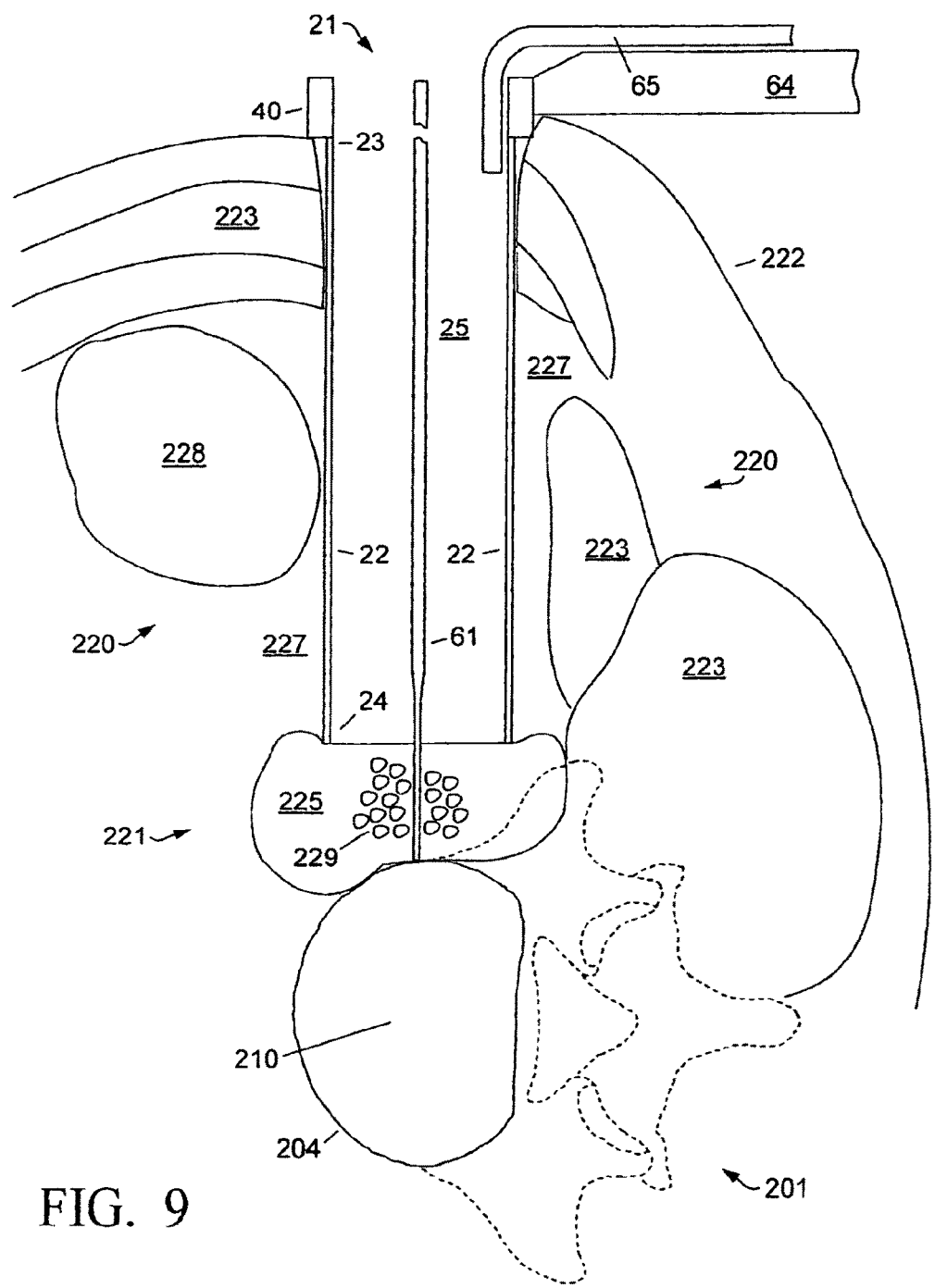
FIG. 9 is a longitudinal section view of a first retractor and a blunt dissector during the forming of an opening in a second tissue.
Figure 10:
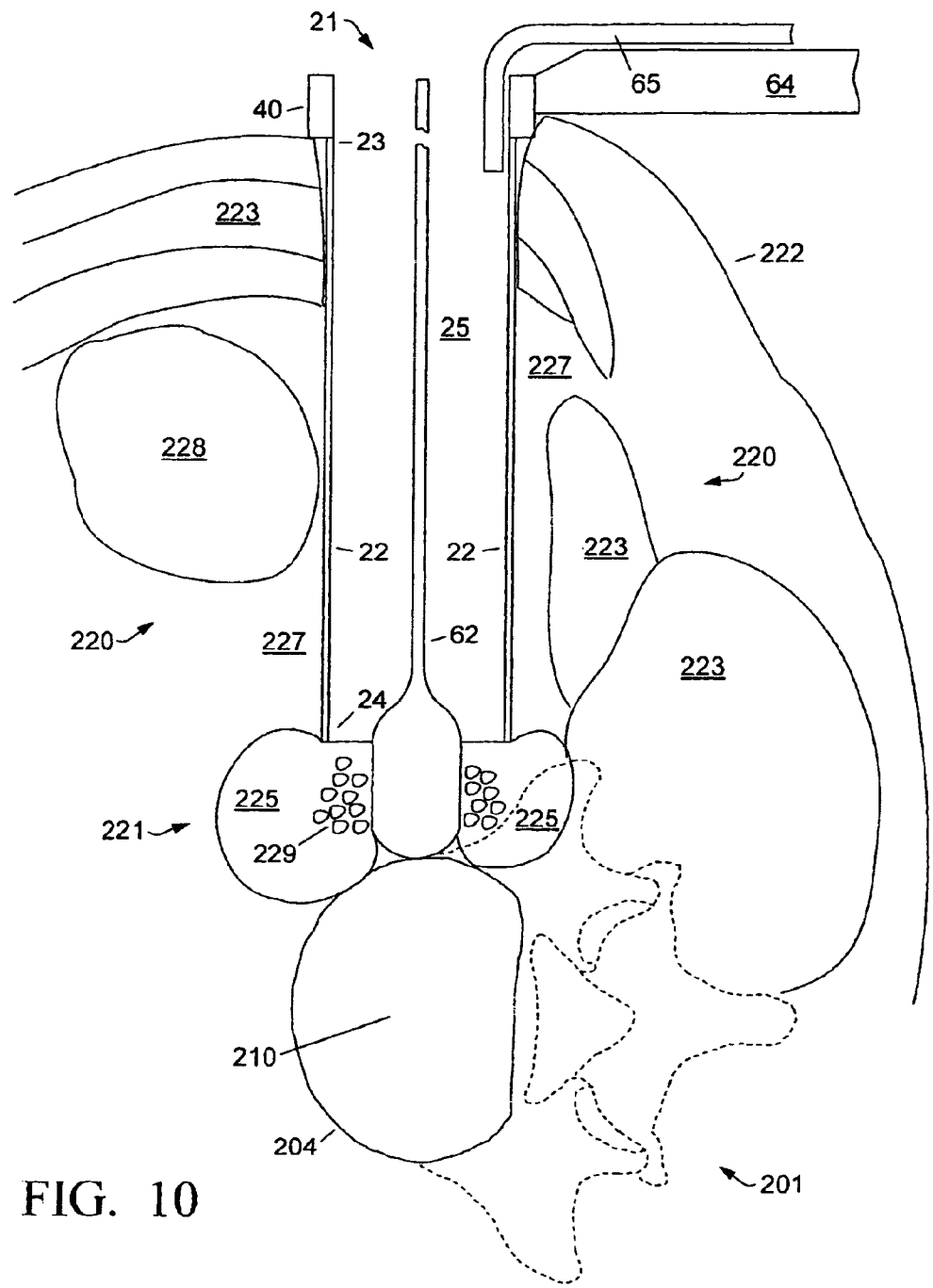
FIG. 10 is a longitudinal section view of a first retractor and a blunt dissector that comprises a spatula after rotation of the spatula to enlarge the opening in the second tissue.
Figure 11:
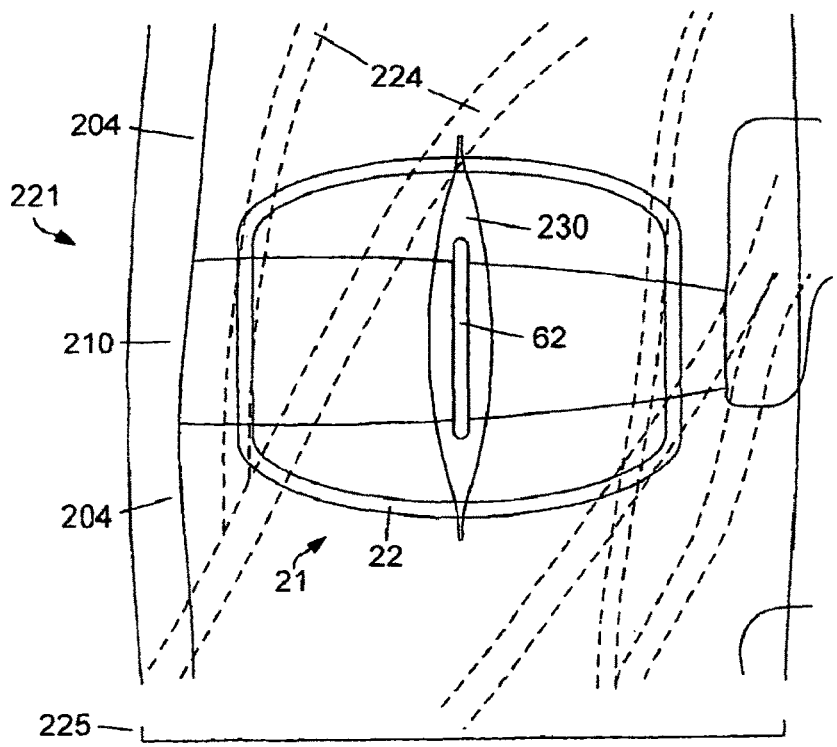
FIG. 11 is a partial section end view of the first retractor, the spatula, and the opening formed by the spatula in the embodiment of FIG. 9.
Figure 12:
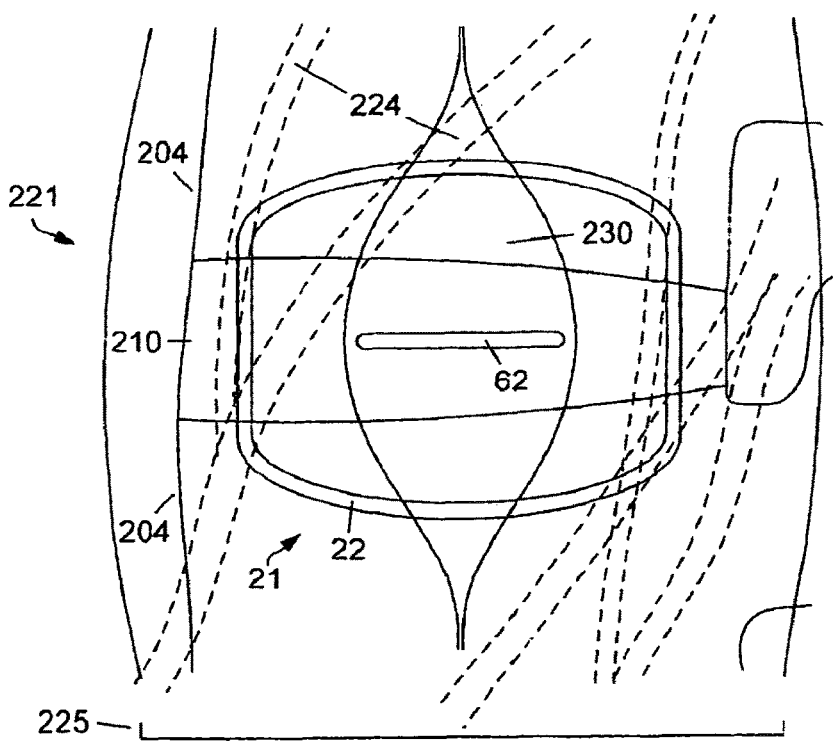
FIG. 12 is a partial section end view of the first retractor, the spatula, and the opening after rotation of the spatula in the embodiment of FIG. 10.

In some embodiments, the method of accessing a surgical site may comprise a step of forming an opening 230 in a second tissue 221, as shown in FIGS. 8-14 (see FIGS. 11-12). FIG. 9 is a longitudinal section view of a first retractor 21 and a blunt dissector 61 during the forming of an opening 230 in a second tissue 221, in accordance with an embodiment.

For example, tissue 221 may be a psoas muscle. As a first step, blunt dissector 61 is pushed into tissue 225 until it contacts disc 210. FIG. 10 shows a longitudinal section view of a first retractor 21 and a blunt dissector 61 that comprises a spatula 62, after rotation of the spatula 62 to enlarge the opening 230 in the second tissue 221.

This is also shown in FIG. 11, which is a partial section end view of the first retractor 21, the spatula 62, and the opening 230 formed by the spatula 62 in the embodiment of FIG. 9. FIG. 12 is a partial section end view of the first retractor 21, the spatula 62, and the opening 230 after rotation of the spatula 62 in the embodiment of FIG. 10.

In the embodiment of FIGS. 9-13, a blunt dissector 61 is used for forming an opening 230 in the second tissue 221 prior to inserting the second retractor 31 into the second tissue 221, as in step (c) of the method. For the embodiment of FIGS. 9-13, inserting the second retractor 31 into the second tissue 221 comprises inserting the second retractor 31 into the opening 230. In another embodiment, an opening 230 may be formed in second tissue 221 using a cutting instrument such as a scalpel or a laser, rather than using a blunt dissector 61.

Blunt dissector 61 may be any type of blunt dissector such as a cylindrical rod or a spatula 62. In the embodiment of FIGS. 9-12, blunt dissector 61 comprises a spatula 62, such as a tool known as a Cobb elevator. A spatula 62 may be inserted into a muscle such as the psoas major muscle 225 with the blade of the spatula 62 parallel to the natural planes within the muscle in order to gently divide the muscle with minimal tearing. After the initial forming of the opening 230, as depicted in FIGS. 9 and 11, the spatula 62 may be rotated to enlarge the opening 230, as depicted in FIGS. 10 and 12.

When the second tissue 221 includes nerves 224, an opening 230 may be initiated and enlarged with careful attention to the nerves 224. Nerves 224 may be damaged if they are stretched, pinched, or severed. Nerves 224 that are beneath the surface of the second tissue 221 may be identified by tactile feedback through the blunt dissector 61 and also by viewing the second tissue 221 during the forming of the opening 230. Nerves 224 are depicted in FIG. 3A and in FIGS. 11-12.

The embodiment of FIGS. 9-13 typically also includes a light source 65, shown in FIG. 9. In the embodiment of FIGS. 9-13, first retractor 21 includes a collar or frame 40 attached to the first retractor's proximal end 23. The collar or frame 40 may be attached to an arm 64 which is secured to the surgical table to stabilize first retractor 21. A light source 65 may be mounted on the arm 64 or on the collar or frame 40. The light source 65 may shine down into first working channel 25 from above, as depicted in FIGS. 9-13. In another embodiment, light source 65 may extend further within first working channel 25 or second working channel 35 so that light is emitted nearer to the second tissue 221 or nearer to the surgical site.

In some embodiments, the method of accessing a surgical site may comprise a step of viewing the second tissue 221 through the first working channel 25 prior to or during the forming of an opening 230 in the second tissue 221. Viewing of the second tissue 221 or the surgical site through the first working channel 25 may include the use of a loupe or surgical microscope or other optical tools, with the assistance of light emitted from light source 65. The ability to view internal surfaces with good illumination and minimal obstruction by devices is an important improvement provided by this invention. For example, one can visualize the tissue at the end of at least said first channel through said first passageway, in the embodiment of FIG. 13.

Figure 13:
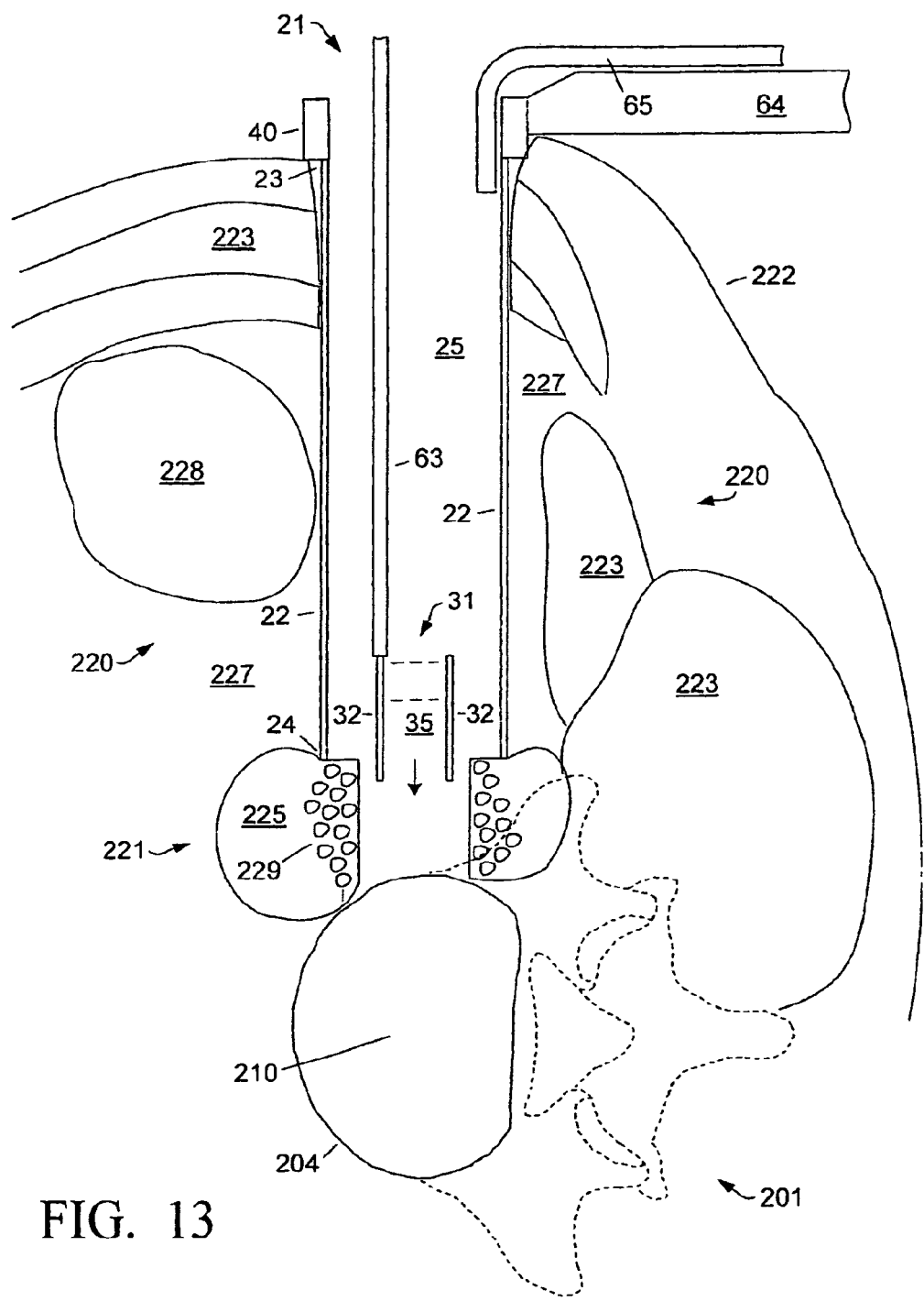
FIG. 13 is a longitudinal section view of a first retractor and a second retractor during the advancing of the second retractor through the first working channel and the inserting of the second retractor into the second tissue.

FIG. 13 is a longitudinal section view of an embodiment showing a first retractor 21 and a second retractor 31 during the advancing of the second retractor 31 through the first working channel 25 and the inserting of the second retractor 31 into the second tissue. FIG. 14 is a longitudinal section view of a surgical retractor system 10 comprising a first retractor 21 and a second retractor 31 after the inserting of the second retractor 31 into the second tissue 221. An inserter 63 (FIG. 13) may be used to manipulate the second retractor 31 during the advancing and the inserting of the second retractor 31.

As depicted in FIGS. 13 and 14, a method comprises inserting the second retractor 31 into a second tissue 221 to retract the second tissue 221 while positioning the second retractor 31 adjacent the first retractor distal end 24. In FIG. 14, the positioning of the second retractor 31 includes positioning the second retractor proximal portion 33 to be external to the first working channel 25 or to be within the first working channel distal region 28. In this embodiment, the first retractor 21 remains proximal to the second tissue 221 during the inserting of the second retractor 31. The positioning of second retractor 31 is described in more detail in connection with FIGS. 4-6. First retractor 21 usually does not intrude into second tissue 221, but instead remains proximal to second tissue 221. Preferably the first working channel distal region 28, which may overlap the second retractor 35, corresponds to no more than about the distal-most 30 percent of the first working channel.

In the embodiment of FIG. 14, a tool 60 is received within first working channel 25 and second working channel 35. In the FIG. 14 embodiment, the tool 60 is an inserter for an intervertebral spacer 66 (a prosthetic implant) that is being installed within the spinal disc 210. In the embodiment of FIG. 1, the depicted tool 60 is a curette. A curette and other tools 60 may be used to prepare a spinal disc 210 for installation of an intervertebral spacer 66. Various tools 60 may be used with surgical retractor system 10, each tool being received within first working channel 25 and second working channel 35. In the example of spine surgery, tools 60 may be used, for example, to treat a vertebra 201 or a spinal disc 210, or to install a prosthetic implant within or adjacent a spine.

In some embodiments, the method of accessing a surgical site may comprise a step of advancing a prosthetic implant through the first working channel 25 and through the second working channel 35. FIG. 14 depicts an embodiment in which a prosthetic implant, such as an intervertebral spacer 66, has been advanced through the first working channel 25 and through the second working channel 35 using an inserter tool 60. The prosthetic implant is positioned within spinal disc 210.

In some embodiments, the method of accessing a surgical site may comprise a step of viewing the second tissue 221 through the first working channel 25 prior to advancing the second retractor 31 through the first working channel 25. In some embodiments, the method of accessing a surgical site may comprise a step of viewing the second tissue 221 through the first working channel 25 during the inserting of the second retractor 31 into the second tissue 221.

In some embodiments, second means for retracting 32 may be expandable, as described in connection with FIGS. 15-35. In some embodiments, the method of accessing a surgical site may comprise a step of expanding the second retractor 31 after inserting the second retractor 31 into the second tissue 221. The second retractor 31 may be expanded using various means such as means described in connection with FIGS. 15-35. In the embodiment of FIG. 13, the second retractor 31 is narrower than the opening 230 in the second tissue 221 during the inserting of the second retractor 31 into the second tissue 221. The second retractor 31 may be expanded after the inserting so that it fills the opening 230. In other embodiments, such as that of FIG. 30, the second retractor 31 may be inserted snugly into a second tissue 221 with subsequent expansion of the second retractor 31, the expansion causing further retraction of the second tissue 221.

In another embodiment which differs from the FIG. 9-13 embodiment, no opening 230 is formed in second tissue 221 prior to inserting the second retractor 31 into the second tissue 221. In such an embodiment, second retractor 31 may comprise a pair of closely apposed blades 41 which serve as a second means for retracting 32. The closely apposed blades 41 may also serve as a means for dissecting or cutting the second tissue 221, so that the inserting of second retractor 31 into second tissue 221 occurs simultaneously with the forming of an opening 230. After the inserting of the second retractor 31 into second tissue 221, the blades 41 may be spread apart, with expanding of the second retractor 31, to create a second working channel 35 between the blades 41.

FIG. 15 is a partial section end view of a surgical retractor system 10 comprising a first retractor 21 and a second retractor 31, the second retractor 31 comprising a jackscrew 50 and a second means for retracting that comprises a plurality of blades 41, in accordance with an embodiment.

FIG. 16 is a partial section end view of the surgical retractor system 10 of FIG. 15 after expanding the second retractor 31. The plurality of blades 41 have moved apart, thereby enlarging the first working channel 35.

FIG. 17 is a side view of the second retractor 31 of the surgical retractor system 10 of FIG. 15, with a driver 67 engaging the jackscrew 50. Rotation of the driver 67 may be used to adjust the distance between the plurality of blades 41 for expanding or contracting second retractor 31.

In the FIG. 16 embodiment, first retractor 21 comprises a track 47 and a pin 54 that is slidably received within track 47. The track 47 and the pin 54 are elongate elements that extend for part or all of the distance between first retractor proximal end 23 and first retractor distal end 24. Pin 54 may be inserted into vertebra 201 (see FIG. 14) in order to stabilize first retractor 21. Another example of a track 47 is depicted in the FIG. 28-30 embodiment.

FIG. 18 is a perspective view of a blade 41 having a curved portion 43, in accordance with an embodiment. A curved portion 43 at the tip of a blade 41 (for example, at 34 in FIG. 17) may help to retract tissue, and a curved portion 43 may be used in any embodiment of a first retractor 21 and in any embodiment of a second retractor 31. FIG. 19 is a perspective view of a blade 41 having a curved portions 43 separated by a cutout 44, in accordance with an embodiment. A cutout 44 may be useful when a first retractor 21 or a second retractor 31 contacts an object whose surface is curved or irregular. For example, a first retractor 31 may be seated against a surgical site that includes a vertebral body 204. The vertebral body 204 generally is somewhat curved and the surface may be irregular because of osteophytes.

Figure 20:
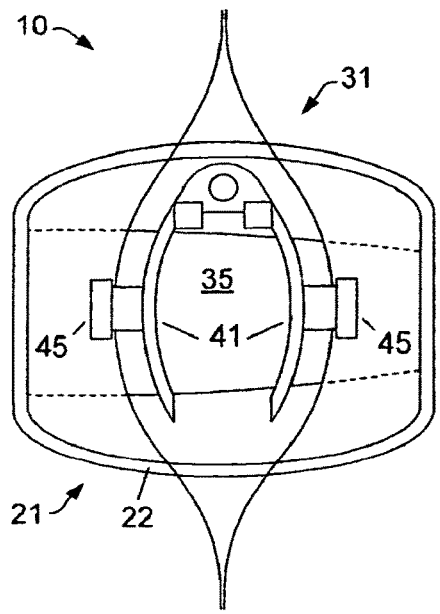
FIG. 20 is a partial section end view of a surgical retractor system comprising a first retractor, a second retractor, and an inserter for manipulating the second retractor, the second retractor comprising tabs for engaging the inserter.
Figure 21:
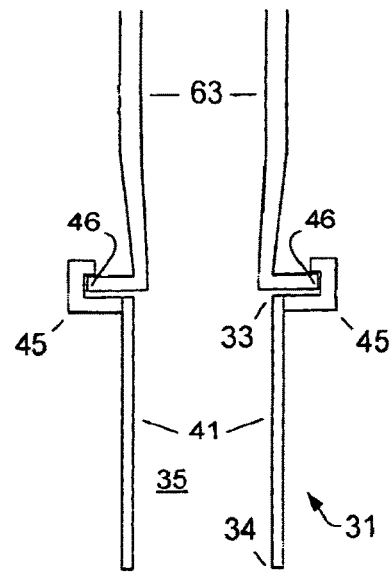
FIG. 21 is a longitudinal section view of the second retractor of the surgical retractor system of FIG. 20, with the inserter engaging grooves in tabs on the second retractor.

FIGS. 20 and 21 depict views of a surgical retractor system 10 comprising a first retractor 21, a second retractor 31, and an inserter 63 for manipulating the second retractor 31, the second retractor 31 comprising tabs 45 for engaging the inserter 63. A distal portion of an inserter 63 is depicted in FIG. 21, and another inserter 63 is depicted in FIG. 13. Inserter 63 may be used for manipulating the second retractor 31 in various ways, including advancing, inserting, repositioning, and removing of the second retractor 31. FIG. 21 is a longitudinal section view of the second retractor 31 of the surgical retractor system 10 of FIG. 20, with the inserter 63 engaging grooves 46 in tabs 45 on the second retractor 31.

Inserter 63 in the FIG. 20-21 embodiment includes a pair of members, the distal end of each member engaging one of the tabs 45 of second retractor 31. The spacing of the members may be adjusted narrower or wider in order to engage the grooves 46 and also to disengage from the grooves 46. For example, the members may be linked by a resilient linkage, so that the inserter 63 is similar to a forceps, or the inserter 63 may be a scissoring type of instrument with a pair of handles that control the spacing of the members. In other embodiments, inserter 63 may engage second retractor 31 through other means such as a threaded connection or a jaw that grips a portion of the second retractor 31.

Figure 22:
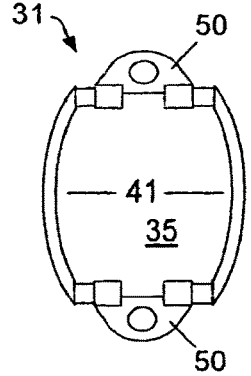
FIG. 22 is an end view of a second retractor comprising plural jackscrews.

FIG. 22 is an end view of a second retractor 31 comprising plural jackscrews 50. As described in connection with the embodiment of FIGS. 15-17, a jackscrew 50 may be used for expanding or contracting second retractor 31. It may be advantageous in some situations to have more than one jackscrew or other mechanism to exert force upon the blades 41. For a second retractor 31 that includes plural jackscrews 50 or other means for expanding or contracting, it may be useful to drive the plural jackscrews synchronously using, for example, a geared mechanism.

Figure 23:
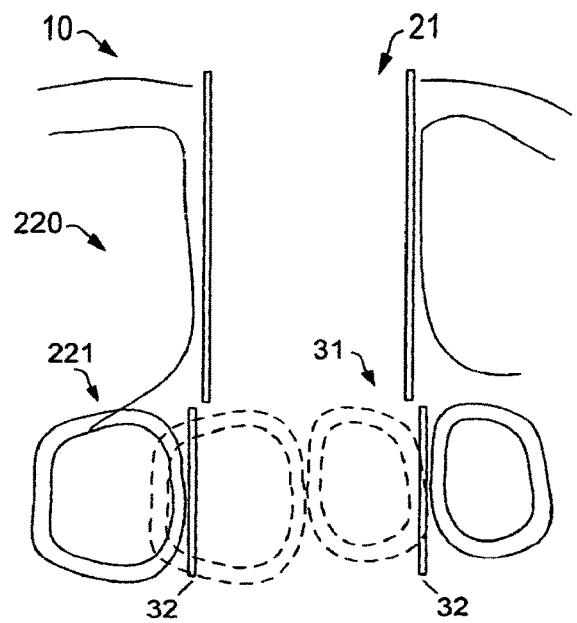
FIG. 23 is a longitudinal section view of a surgical retractor system comprising a first retractor and a second retractor, before and after expanding the second retractor.

FIG. 23 is a longitudinal section view of a surgical retractor system 10 comprising a first retractor 21 and a second retractor 31, after expanding the second retractor 31, in accordance with an embodiment. In the FIG. 23 embodiment, the second retractor 31 is expanded to have a transverse dimension that is greater than or equal to the transverse dimension of the first retractor 21. The dashed outlines indicate the position of the second tissue 221 prior to retraction by the second retractor 31. The second retractor 31 may be contracted, reversing the expansion, for removal through first retractor 21.

For a surgical retractor system 10 as shown in FIG. 23, second retractor 31 may be inserted into a second tissue 221 after the advancing of the second retractor 31 through the first working channel 25. The second retractor 31 has a second retractor transverse dimension that is sized to permit the advancing of the second retractor 31 through the first working channel 25.

The second retractor 31 may have an expanded transverse dimension that is different from the initial transverse dimension during the advancing through the first working channel 25.

Figure 24:
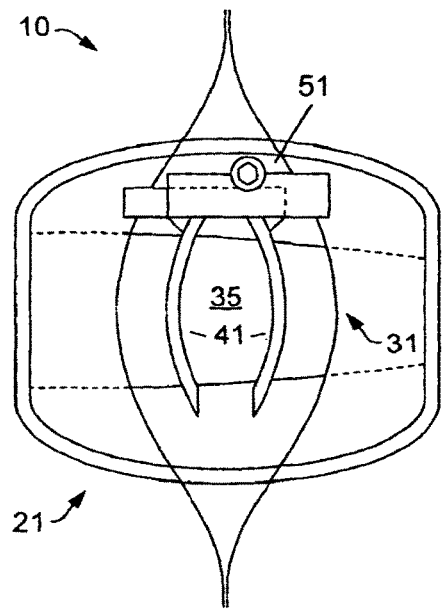
FIG. 24 is a partial section end view of a surgical retractor system comprising a first retractor and a second retractor, the second retractor comprising a rack and pinion and a second means for retracting that comprises a plurality of blades.
Figure 25:
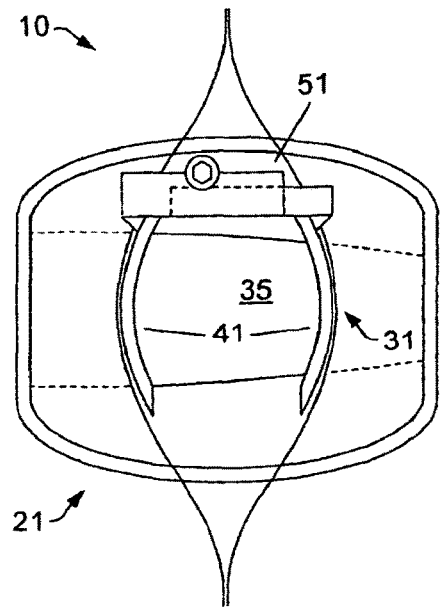
FIG. 25 is a partial section end view of the surgical retractor system of FIG. 24 after expanding the second retractor.

FIG. 24 is a partial section end view of a surgical retractor system 10 comprising a first retractor 21 and a second retractor 31, the second retractor 31 comprising a rack and pinion 51 and a second means for retracting that comprises a plurality of blades 41, in accordance with an embodiment. The rack and pinion 51 is attached to one end of each blade 41 at the upper edge of the blade 41, so that the rack and pinion 51 is held above the second tissue 221 by the blades 41. A driver, such as the driver 67 depicted in FIG. 17, may be used to rotate the pinion in the rack and pinion 51 to adjust the distance between the plurality of blades 41 for expanding or contracting second retractor 31. FIG. 25 is a partial section end view of the surgical retractor system 10 of FIG. 24 after expanding the second retractor 31.

Figure 26:
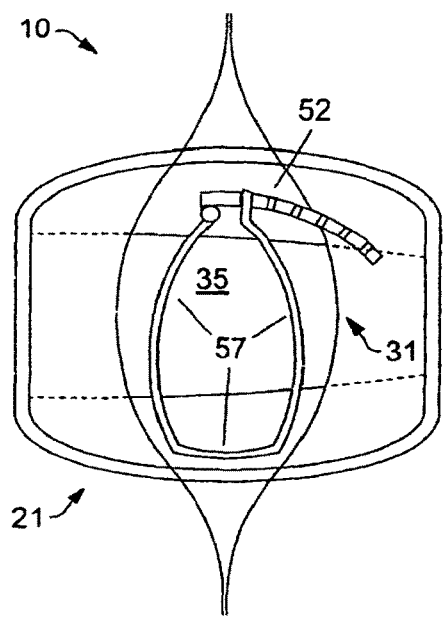
FIG. 26 is a partial section end view of a surgical retractor system comprising a first retractor and a second retractor, the second retractor comprising a ratchet and a second means for retracting that is U-shaped.
Figure 27:
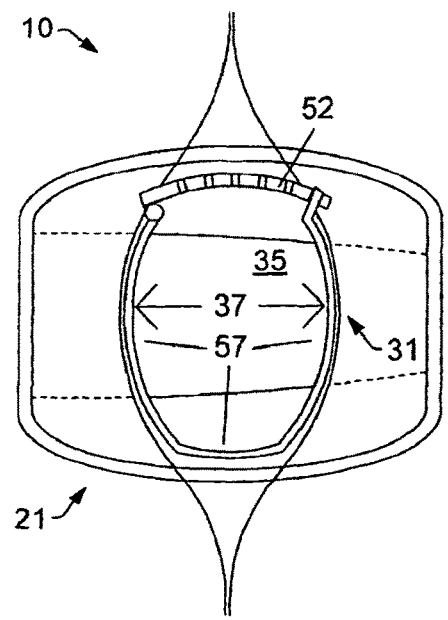
FIG. 27 is a partial section end view of the surgical retractor system of FIG. 26 after expanding the second retractor.

FIG. 26 is a partial section end view of a surgical retractor system 10 comprising a first retractor 21 and a second retractor 31, the second retractor 31 comprising a ratchet 52 and a second means for retracting 57 that is U-shaped, in accordance with an embodiment. The ratchet 52 includes an arc that is attached to one end of the U-shaped second means for retracting 57 and a pin that engages the arc, the pin being attached to a second end of the U-shaped means for retracting 57. The ratchet 52 is attached at the upper edge of the U-shaped means for retracting 57, so that the ratchet 52 is held above the second tissue 221 by the U-shaped means for retracting 57. FIG. 27 is a partial section end view of the surgical retractor system 10 of FIG. 26 after expanding the second retractor 31. The second working channel diameter 37 is indicated.

Figure 28:
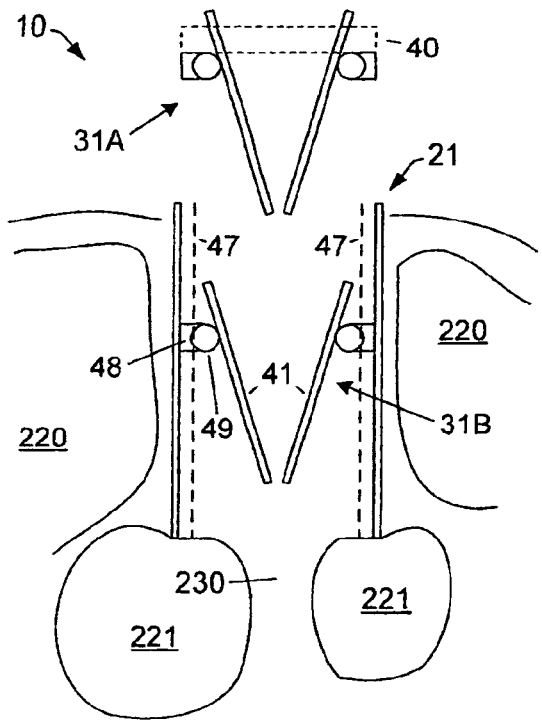
FIG. 28 is a longitudinal section view of a surgical retractor system comprising a first retractor and a second retractor that is removably attachable to the first retractor.

FIG. 28 is a longitudinal section view of a surgical retractor system 10 comprising a first retractor 21 and a second retractor 31 that is removably attachable to the first retractor 21, in accordance with an embodiment. In FIG. 28, second retractor 31 is depicted at two positions which correspond to two time points: second retractor 31A is depicted before the attaching to first retractor 21, and second retractor 31B is depicted during the advancing of the second retractor 31B.

In the FIG. 28 embodiment, first retractor 21 comprises one or more tracks 47, preferably plural tracks 47. In the FIG. 28 embodiment, a second means for retracting comprises a plurality of blades 41. As indicated for second retractor 31A, second retractor 31 may comprise a frame or collar 40 that links the blades 41. Each blade 41 is attached to the first retractor 21 through a pivot 49 and a means for attaching which comprises a connector 48. The means for attaching (connector 48) is slidable along track or tracks 47. During the advancing of the second retractor 31 through the first working channel 25, the blades 41 are tilted inwards at second retractor distal end 34, to facilitate insertion of the second retractor 31 into the second tissue 221. In another embodiment, blades 41 may have a fixed upright orientation, rather than being tilted initially.

Figure 29:
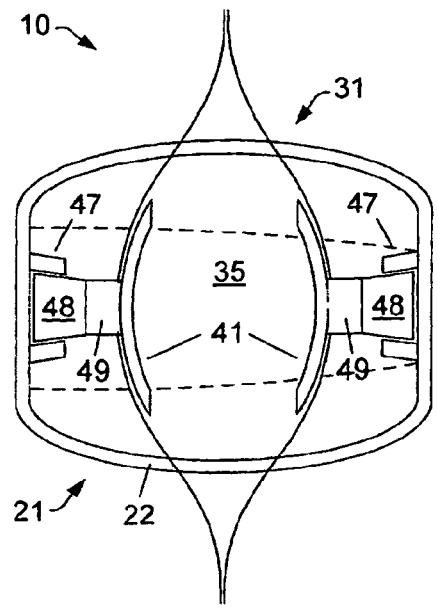
FIG. 29 is a partial section end view of the surgical retractor system of FIG. 28.
Figure 30:
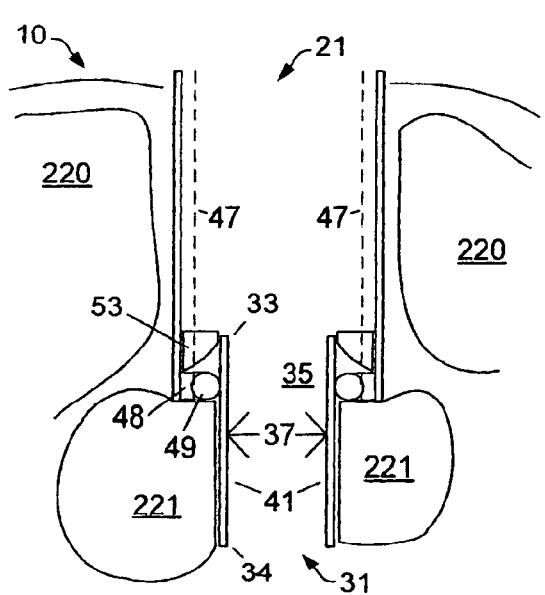
FIG. 30 is a longitudinal section view of the surgical retractor system of FIG. 28 after the inserting of the second retractor into the second tissue.

FIG. 29 is a partial section end view of the surgical retractor system 10 of FIG. 28 after the inserting of the second retractor 31 into the second tissue 221. The blades 41 have been rotated so that they are no longer tilted. FIG. 30 is a longitudinal section view of the surgical retractor system 10 of FIG. 28 after the inserting of the second retractor 31 into the second tissue 221, in accordance with an embodiment. The blades 41 have been rotated so that they are no longer tilted. A means for locking 53 secures the blades 41 in the upright (not tilted) orientation. In an embodiment, the blades 41 can be further tilted to expand the distal opening (see FIG. 45D, for example). In the FIG. 30 embodiment, means for locking 53 is a wedge that may be inserted from above. For example, means for locking 53 may be a wedge that slides within track 47 and that is attached to a shaft that extends upward for manipulation of the means for locking 53.

Figure 31:
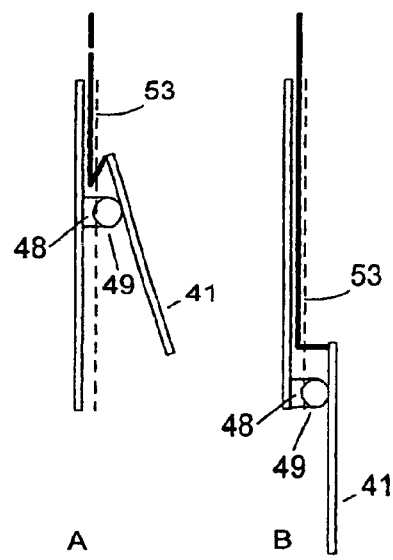
FIG. 31 is a longitudinal section view of a portion of a surgical retractor system similar to that of FIGS. 28-30.

FIG. 31 is a longitudinal section view of a portion of a surgical retractor system 10 similar to that of FIGS. 28-30, in accordance with an embodiment. FIG. 31 includes two views A and B, which correspond to different states of the means for locking 53. In view A, the blades 41 are tilted and means for locking 53 is in the unlocked (collapsed) state. In view B, the blades 41 are rotated so that they are no longer tilted, and means for locking 53 is in the locked state. In the FIG. 31 embodiment, the means for locking 53 is a rotatable arm attached to a shaft that extends upward for manipulation of the means for locking 53. The shaft within means for locking 53 may be secured at a specific vertical position relative to first retractor 21 using, for example, a pin or a threaded nut.

In other embodiments, second retractor 31 may be removably attachable to first retractor 21 using other means for attaching. The means for attaching may include, for example, a pin on the second retractor 31 that engages a dimple or hole on the inner surface of first means for retracting 22. The means for attaching may include, for example, an elongate hanger for suspending the second retractor 31 within first working channel 25, the hanger extending between the second retractor 31 and a proximal location on first retractor 21.

Figure 32:
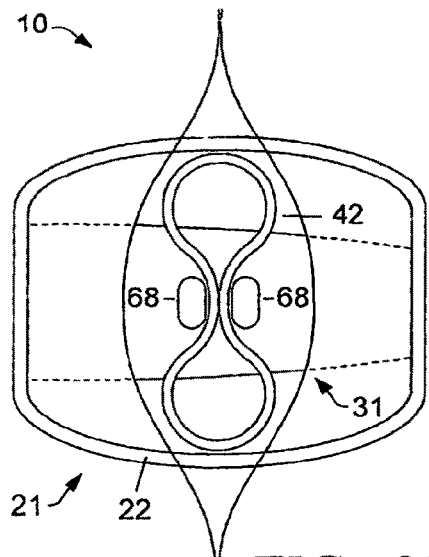
FIG. 32 is a partial section end view of a surgical retractor system comprising a first retractor and a second retractor, the second retractor comprising a second means for retracting that comprises a flexible tube.
Figure 33:
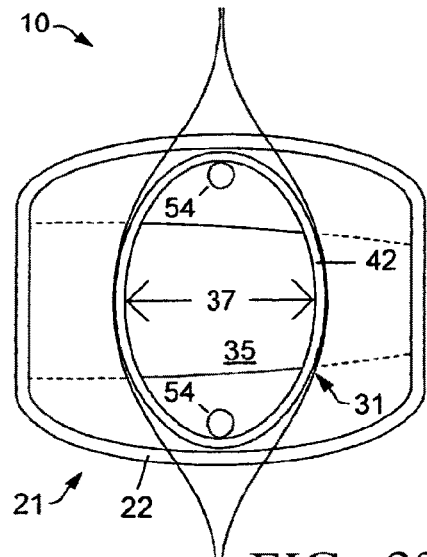
FIG. 33 is a partial section end view of the surgical retractor system of FIG. 32 after expanding the second retractor by withdrawing the inserter.
Figure 34:
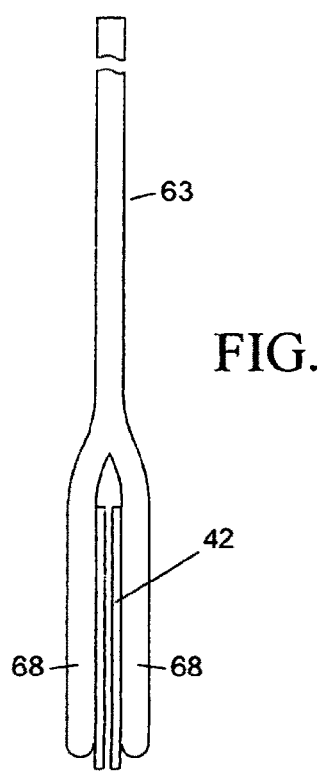
FIG. 34 is a longitudinal section view of the flexible tube and the inserter of the surgical retractor system of FIG. 32.

FIG. 32 is a partial section end view of a surgical retractor system 10 comprising a first retractor 21 and a second retractor 31, the second retractor 31 comprising a second means for retracting that comprises a flexible tube 42, in accordance with an embodiment. In other embodiments, tube 42 may not be flexible. FIG. 32 depicts second retractor 31 (flexible tube 42) during the insertion of second retractor 31 into the second tissue 221. Flexible tube 42 is held by the prongs 68 of a forked inserter 63 (see FIGS. 34-35). FIG. 33 is a partial section end view of the surgical retractor system 10 of FIG. 32 after expanding the second retractor 31 by withdrawing the inserter 63. FIG. 34 is a longitudinal section view of the flexible tube 42 and the inserter 63 of the surgical retractor system 10 of FIG. 32. The prongs 68 of the inserter 63 grip the flexible tube 42 and compress it.

Figure 35:
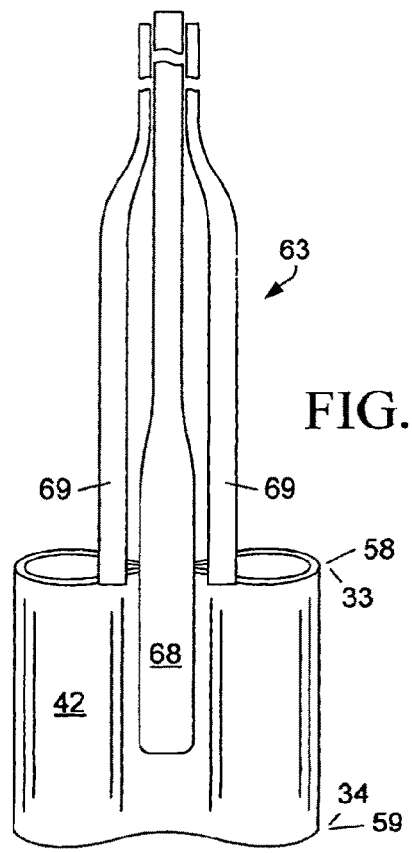
FIG. 35 is a perspective side view of the flexible tube and the inserter of the surgical retractor system of FIG. 32.

FIG. 35 is a perspective side view of the flexible tube 42 and the inserter 63 of the surgical retractor system 10 of FIG. 32. Inserter 63 includes a second pair of members 69 that are capable of moving relative to the long dimension of inserter 63. To release flexible tube 42 from inserter 63 after flexible tube 42 is inserted into second tissue 221, prongs 68 are pulled upward while members 69 push down on the second means for retracting proximal end 33 (i.e., the top of the flexible tube 42). The FIG. 33 embodiment includes pins 54 that are inserted into each vertebra 201. The pins 54 pass just inside of flexible tube 42 and may serve to stabilize second retractor 31 (flexible tube 42). Pins 54 may be slidably received within tracks 47 in first retractor 21, as described in connection with FIG. 16.

FIG. 36 is a partial section end view of a surgical retractor system 10 comprising a first retractor 21, a second retractor 31, and a set of sequential dilators 55, the second retractor 31 comprising a second means for retracting that comprises a tube 42, in accordance with an embodiment. In the embodiment of FIG. 36, the set of sequential dilators 55 comprises three sequential dilators 55A, 55B, and 55C. In the FIG. 36 embodiment, a first one 55A of the set of sequential dilators comprises a spatula. Tube 42 is sized for insertion over a final one 55C of the set of sequential dilators 55. FIG. 37 is a partial section end view of the surgical retractor system 10 of FIG. 36 after removal of the sequential dilators 55.

FIG. 38 is a longitudinal section view of the surgical retractor system 10 of FIG. 36 during the insertion of the tube 42 over a final one 55C of the set of sequential dilators 55. The view of FIG. 38 is taken in a plane A-A' of FIG. 36. Tube 42 is advanced by an inserter 63.

FIG. 39 is a partial section end view of a surgical retractor system 10 similar to that of FIGS. 36-38 after removal of the sequential dilators 55, the surgical retractor system 10 including a pin 54, in accordance with an embodiment. The pins 54 may serve to stabilize second retractor 31 (tube 42). Pins 54 may be slidably received within tracks 47 in first retractor 21, as described in connection with FIG. 16.

FIG. 40 is a partial section end view of a surgical retractor system 10 comprising a first retractor 21 and a second retractor 31, the first retractor 21 comprising a first means for retracting that comprises a tube 42, in accordance with an embodiment. In the embodiment of FIG. 40, the tube 42 has a cross-sectional shape that is a rounded square. FIG. 41 is a partial section end view of a surgical retractor system 10 comprising a first retractor 21 and a second retractor 31, the first retractor 21 comprising a first means for retracting 22 that comprises a tube 42, in accordance with an embodiment. In the embodiment of FIG. 40, the tube 42 has a cross-sectional shape that is a circle.

FIG. 42 is a partial section end view of a surgical retractor system 10 comprising a first retractor 21 and a second retractor 31, the first retractor 21 comprising a first means for retracting that comprises a plurality of blades 41A, in accordance with an embodiment. In the embodiment of FIG. 42, the plurality of blades 41A comprises three blades 41A. The first working channel diameter 27 is indicated. In some embodiments, first means for retracting 21 may be expandable. In the embodiment of FIG. 42, for example, first means for retracting 21 comprises a plurality of blades 41A which are depicted after expanding of first retractor 21 by moving apart blades 41A. In some embodiments, the method of accessing a surgical site may comprise a step of expanding the first retractor 21 after inserting the first retractor 21 into the first tissue 220.

In FIG. 43, several distal-most percentages are indicated as fractions. For example, the fraction 0.8 indicates 80 percent, and the fraction 0.1 indicates 10 percent. For example, first working channel distal region 28 may correspond to less than or equal to the distal-most 80, 70, 60, 50, 40, 30, 20, 10, or 5 percent of the first working channel 25. In the second retractor 31 embodiment depicted in FIG. 43, second means for retracting proximal portion 38 is relatively long compared to first working channel 25, so that first working channel distal region 28 corresponds to less than or equal to the distal-most 80 percent (indicated as fraction 0.8) of first working channel 25. In other embodiments, first working channel distal region 28 may correspond to less than or equal to a smaller percentage (fraction) of first working channel 25, as indicated by the fractions depicted in FIG. 43.

Figure 44:
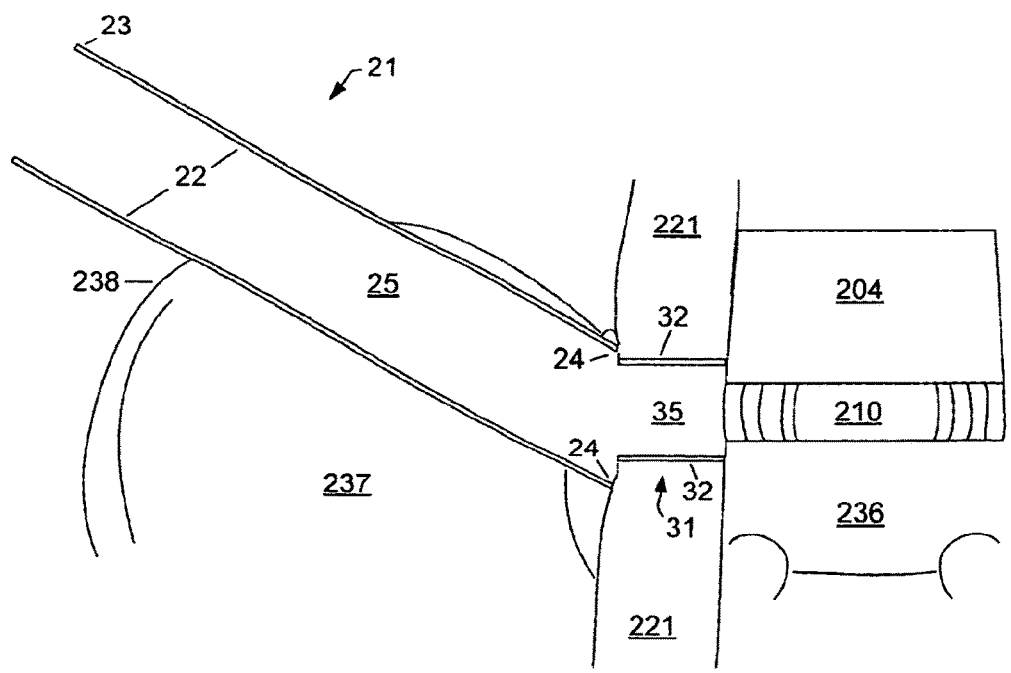
FIG. 44 is a longitudinal section view of a surgical retractor system comprising a first retractor and a second retractor, in which the first means for retracting has a distal end which is beveled.
Figure 45D:
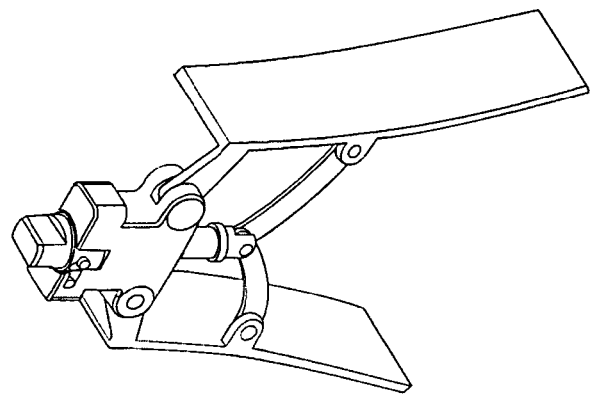
FIG. 45A, FIG. 45B, FIG. 45C and FIG. 45D show a sequence of cartoons depicting the passage of a retractor through a tube and its deployment at an internal site.
Figure 45C:
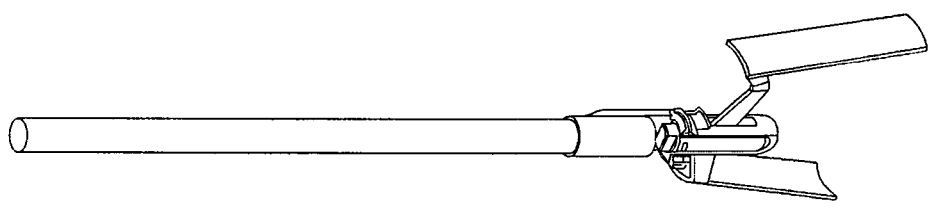
Figure 45B:
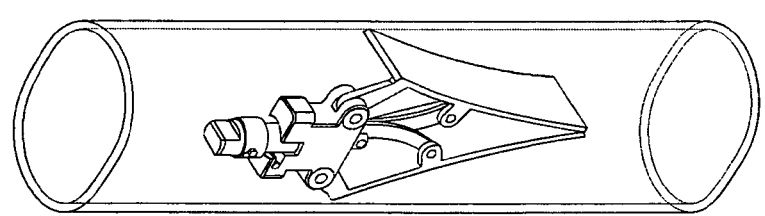
Figure 45A:
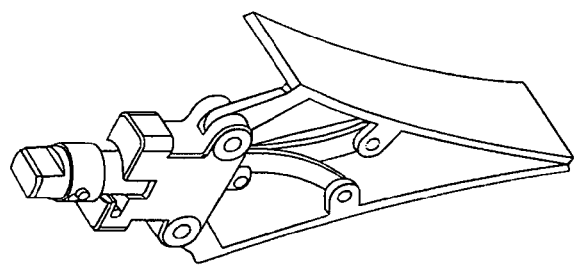

FIG. 44 is a longitudinal section view of a surgical retractor system 10 comprising a first retractor 21 and a second retractor 31, in which the first retractor distal end 24 is beveled, in accordance with an embodiment. The beveled first retractor distal end 24 facilitates an oblique surgical approach to a surgical site that is partially obstructed by another element. In the FIG. 44 embodiment, second tissue 221 is a muscle lateral to a spine. The surgical site in the spine, in this example, includes a spinal disc 210 that is between a vertebral body 204 (e.g. lumbar vertebra L5) and a second body, e.g. sacrum 236, which is part of the pelvis.

A lateral approach to this particular spinal disc 210, using an orientation that is perpendicular to the spine axis, is obstructed by the ilium 238 of the pelvis. To circumvent the ilium 238, first retractor 21 is oriented obliquely to the spine axis, passing above the iliac crest 238 and aiming obliquely downward to dock upon the second tissue (muscles) 221. The beveled first means for retracting distal end 24 facilitates docking of first retractor 21 upon second tissue 221 and facilitates the inserting of second retractor 31 into second tissue 221. First retractor 21 may be attached to an arm (not shown) which is secured to the surgical table to stabilize first retractor 21, as described in connection with the embodiment of FIGS. 9-13.

This site is a common site needing treatment, but this lower trauma approach is not accessible with conventional systems.

FIG. 45 shows the process of deployment of a retractor pair of the invention. Panel A shows a retractor in its non-expanded form, with its two blades touching at their tips. In Panel B, the retractor of Panel A, as a second retractor, is passed (using conveying means, not shown) through a first, tubular retractor, in this case in the preferred form (straight sides, round shoulders), which may be flexible enough to be round (approximately circular) during delivery. In Panel C, a device is applied to the second retractor, opening up the blades. In Panel D, the deployed retractor is shown. This process is reversed to remove the retractors after the completion of the procedure. A preferred feature is seen in Panel D of FIG. 45, in which the opened-up retractor has a separation in the blades which progresses from widest at the distal points, and narrowing in the blade separation at the proximal end. This orientation is reversed (Panel B) or evened out (not illustrated) as the retractor is inserted and removed.

Moreover, the ability to perform this reversal makes the use of a blade-type retractor as the second retractor to be a preferred alternative, compared to the use of a tubular retractor. This is because the limiting diameter of a tube is more difficult to expand when it is the second, more distal retractor. Moreover, the bladed reactor of FIG. 45 offers a built-in retention capacity when it is expanded while at or near the most distal site of its deployment, because to the extent that it displaces any tissue (for example by having the tips slide along a bone as the retractor is expanded), the tissue will tend to press on the retractor blades, forcing them against the bone or other structure, and in doing so, tending to prevent the displacement of the retractor towards the proximal end of the site until the procedure is completed, and the retractor is retracted.

There is a preference towards use of a tube, preferably of the "square with rounded corners" type, as the first retractor. This is because expansion over sequentially introduced nesting dilating tubes can be fast and minimally traumatic. However, especially if the proximal span of the first retractor can be short, a blade type retractor can be effective as the first retractor in the practice of the invention.

In any of these embodiments, various procedures can be used to enhance tissue separation at any or all of the creation of a passage for said first retractor, or said for second retractor, or for purposes of the procedure at tissue distal of said second retractor.

Retractor Insertion and Deployment

Adjustable retractors are normally applied directly to a surgical site accessible from outside the body, and can be adjusted to an expanded state, and later collapsed with the mechanism of retraction, such as screw or ratchet, located outside the body. At greater depths within the body, this requires a powerful mechanism with bulky and rigid blades. In the retractor systems of the invention, conventional adjustable retractors used as second retractors can be applied with the mechanism of retraction at depths of ten centimeters or more in the body A first type of custom retractor adjuster was developed from a section of a hexagonal wrench bonded to the tip of a flexible shaft. However, torque control with strictly manual methods can be difficult, and it is difficult to precisely control the orientation of the retractor while it is being expanded.

Figures 46A, 46B, 46C:
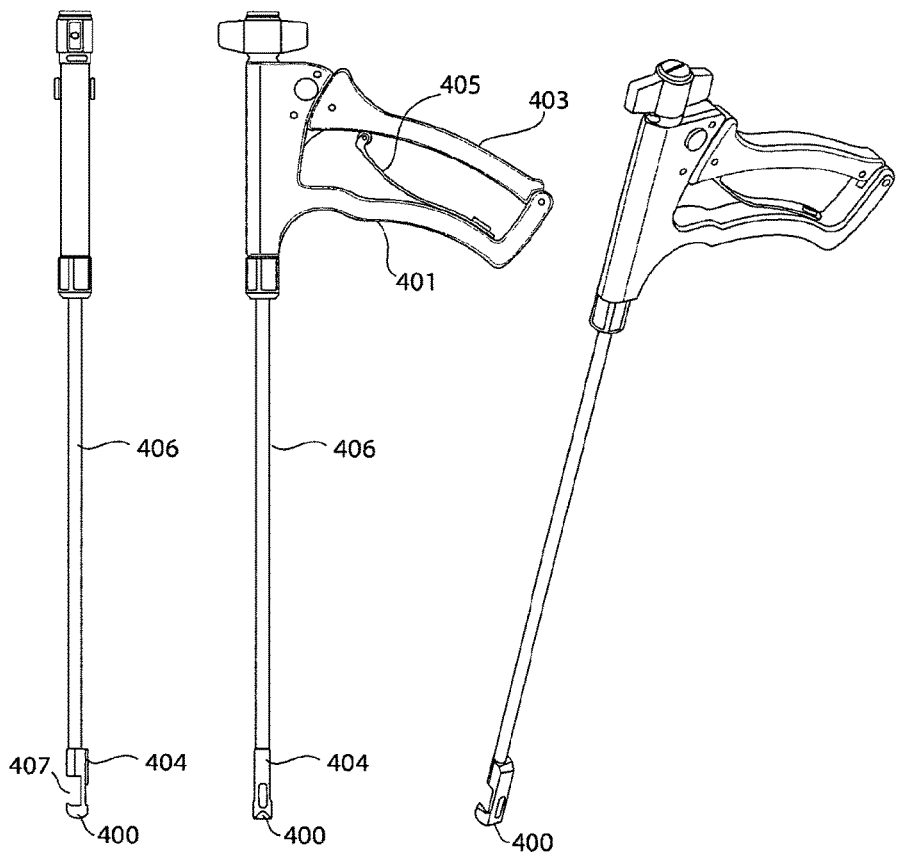
FIG. 46A, FIG. 46B, FIG. 46C and FIG. 47 show a specialized device for configuring a second retractor deployed in or near the distal end of a first retractor.

An improved retractor inserter has been created, which allows control of placement and retrieval, along with controllable application of torque to the retractor to localize it in situ. FIG. 46 shows an example of the assembled retractor inserter, and FIG. 47 shows the device in exploded view.

The inserter 400 (also shown as 63 in FIG. 45) has a handle 401, and a movable control 403. The control 403, together with a squeezable member 402 (see next figure), allows the hook 407 of distal end 404 of the external fixed shaft 406 to be closed, working against spring 405 by pulling a rod (not seen) to contact the hook 407, by moving distally within fixed shaft 406. The distal end 404 can be seen gripping a retractor in FIG. 45C.

Figure 47:
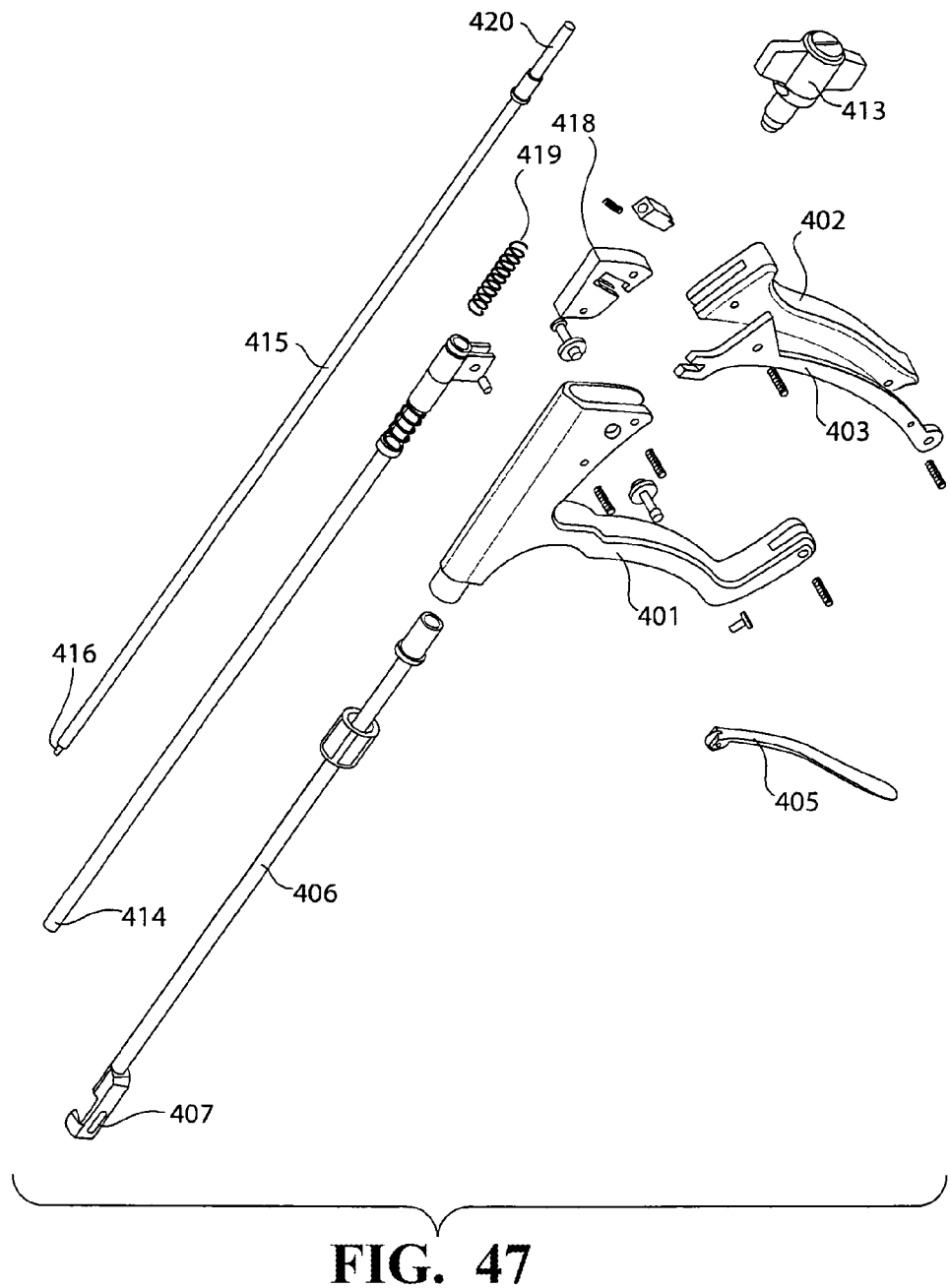

FIG. 47 shows an exploded view of the retractor inserter 400. In addition to the parts named above, the pusher rod assembly 414, riding within shaft 406, and the driver rod assembly 415 riding within pusher rod 414 are shown. The driver rod carries a tip 416 which mates with the adjustment mechanism of the retractor (not shown). Torque is applied to the proximal end 420 of driver rod 415 by torque knob 413.

In use, a retractor for use in the invention is grasped by placing it in the hook 407. It is held there by pressing squeezable member 402. The retractor is then inserted to the site of use, typically through a previously-deployed first retractor, to the site where it is to be used to retract tissue. Once the tips of the blades of the retractor have been placed at a desired location, typically distally of a distal end of a first retractor, then the torque knob 413 is rotated to drive the blades of the retractor to the open state. After the procedure is complete, the retractor is removed by reversing this procedure. Both the retractor and the retractor inserter are at least potentially re-usable, after cleaning and sterilization.

Optional features of the retractor inserter include one-way ratcheting action of the torque knob 413, so that it can expand the retractor with rapid short, partial turns; together with a reversing control or a ratcheting release to allow the retractor to be removed from the site. A second, preferred feature is to place force-limiting features in the torque knob, or in a functionally equivalent position, to limit the force which can be applied to the expansion of the retractor. A simple method is to spring-load the driver rod assembly 415 of FIG. 47, for example with a spring 419 riding against push rod 414 shown in FIG. 47, so that the maximum rotational torque that can be applied to a retractor is limited (rising with the degree of compression of the spring). Such an instrument is normally calibrated before use. Other adjustable torque control or other force limiting mechanisms are known and may be applicable to this device.

The detailed design of a retractor inserter is presented as an example of a highly useful accessory in the system of the invention. The examples show a relatively close alignment of the second retractor relative to the first retractor, but the invention also encompasses greater degrees of divergence. A retractor inserter of the invention can be any retractor inserter which can place a second retractor in a location within the body, wherein said location is characterized in having one or more of orientation, angulation and depth, all relative to a first retractor, that are different from the orientation, angulation and depth of the first retractor.

Additional embodiments of the retractor inserter can be envisaged by the person of ordinary skill, and the use of retractor inserters in surgery, and especially in the surgical procedures of the present invention, is an object of the present invention.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Although we have described in detail various embodiments, those skilled in the art will recognize, or be able to ascertain using no more than routine experimentation, many equivalents to the specific embodiments of the invention described herein. Such equivalents are intended to be by the following claims. Other embodiments and modifications will be apparent to those of skill in the art in light of this text and accompanying drawings. The following claims are intended to include all such embodiments, modifications and equivalents.

What is claimed is:

1. A surgical retractor system, comprising:
    a first retractor having a proximal end and a distal end, wherein the first retractor comprises a tube that can be passed through a tissue site to provide access through a first working channel forming a passage through an interior of the first retractor; and
    a second retractor having a proximal end and a distal end and comprising a pair of blades proximate the distal end of the second retractor, each blade in the pair of blades being concave inward with respect to a second working channel proximal end axis of the blade;
    wherein the second retractor has a first configuration in which the second retractor is dimensioned to be insertable through the first working channel of the first retractor, and wherein the proximal end of the second retractor is positionable in the vicinity of the first retractor distal end, and wherein a distance between the pair of blades can be expanded to form a second working channel through the second retractor while the second retractor proximal end is positioned through the first working channel such that the blades of the second retractor extend beyond the first retractor distal end and both the first retractor and second retractor simultaneously retract tissues and allow surgical access through the first and second working channels.

2. The system of claim 1, wherein the tube comprises a rounded rectangular cross section.

3. The system of claim 1, wherein the pair of blades is located at the distal end of the second retractor.

4. The system of claim 3, where the pair of blades in the first configuration touch one another at their distal tips.

5. The system of claim 4, wherein the distal tips can be moved apart to open the blades.

6. The surgical retractor system of claim 5, wherein the distal tips of the blades are separated by a distance greater than the first working channel of the first retractor in at least one configuration.

7. The system of claim 1, further comprising a retractor inserter coupled to the second retractor.

8. The system of claim 1, further comprising one or more surgical dilators.

9. The system of claim 8, wherein the one or more surgical dilators include a set of dilators.

10. The system of claim 9, wherein the first retractor is sized for insertion over one of the dilators.

11. The system of claim 8, wherein at least one of the dilators is a blunt dissector.

12. The system of claim 11, wherein the blunt dissector comprises a cylindrical rod.

13. The system of claim 1, further comprising an implant, wherein the first retractor is dimensioned to be capable of receiving the implant through the first working channel of the first retractor, and wherein the second retractor is dimensioned to be capable of receiving the implant through the second working channel of the second retractor.

14. The surgical retractor system of claim 1, wherein each blade of the pair of blades curves away from a second working channel proximal end axis from a proximal end to a distal end of the blade.

15. The surgical retractor system of claim 1, wherein the second retractor further comprises a jackscrew connected to the pair of blades to move the blades apart.

16. The surgical retractor system of claim 1, wherein the second retractor further comprises a frame connected to each of the pair of blades at an end portion of a proximal edge of each blade and wherein the frame does not obstruct the second working channel.

17. A surgical retractor system, comprising:
a first retractor having a proximal end and a distal end, wherein the first retractor comprises a tube having a first working channel forming a passage through an interior of the first retractor;
a second retractor having a proximal end and a distal end and comprising a pair of blades proximate the distal end of the second retractor and a means for expanding a distance between the pair of blades, each blade in the pair of blades being concave inward with respect to a second working channel proximal end axis of the blade; and
wherein the second retractor has a first configuration in which the second retractor is dimensioned to be insertable through the first working channel of the first retractor, and wherein the proximal end of the second retractor is positionable in the vicinity of the first retractor distal end, and wherein the means for expanding increases the distance between the pair of blades to form a second working channel through the second retractor while the second retractor proximal end is positioned through the first working channel proximate the first retractor distal end such that both the first retractor and second retractor simultaneously retract tissues, and
wherein the means for expanding does not obstruct the second working channel.

* * * * *